(12) United States Patent
Yamanishi et al.

(10) Patent No.: US 11,730,531 B2
(45) Date of Patent: Aug. 22, 2023

(54) BUBBLE JETTING MEMBER AND METHOD FOR PRODUCING SAME, GAS/LIQUID JETTING MEMBER AND METHOD FOR PRODUCING SAME, LOCALIZED ABLATION DEVICE AND LOCALIZED ABLATION METHOD, INJECTION DEVICE AND INJECTION METHOD, PLASMA-BUBBLE JETTING MEMBER, AND THERAPEUTIC DEVICE AND THERAPEUTIC METHOD

(71) Applicant: JAPAN SCIENCE AND TECHNOLOGY AGENCY, Kawaguchi (JP)

(72) Inventors: Yoko Yamanishi, Nagoya (JP); Shinya Sakuma, Nagoya (JP); Hiroki Kuriki, Nagoya (JP); Fumihito Arai, Nagoya (JP)

(73) Assignee: JAPAN SCIENCE AND TECHNOLOGY AGENCY, Kawaguchi (JP)

(*) Notice: Subject to any disclaimer, the term of this patent is extended or adjusted under 35 U.S.C. 154(b) by 522 days.

(21) Appl. No.: 16/884,365

(22) Filed: May 27, 2020

(65) Prior Publication Data
US 2020/0337757 A1    Oct. 29, 2020

Related U.S. Application Data

(62) Division of application No. 14/382,012, filed as application No. PCT/JP2013/055703 on Mar. 1, 2013, now Pat. No. 10,716,610.

(30) Foreign Application Priority Data

Mar. 2, 2012 (JP) .................................. 2012-047053
Jan. 11, 2013 (JP) .................................. 2013-003748

(51) Int. Cl.
A61B 18/04   (2006.01)
C12N 15/87   (2006.01)
(Continued)

(52) U.S. Cl.
CPC ............ *A61B 18/042* (2013.01); *A61B 18/12* (2013.01); *A61M 5/30* (2013.01); *A61N 1/44* (2013.01);
(Continued)

(58) Field of Classification Search
CPC ........ A61B 18/042; A61B 18/12; A61M 5/30; A61N 1/44; C12M 35/04; C12N 15/87
(Continued)

(56) References Cited

U.S. PATENT DOCUMENTS 3,838,242 A    9/1974   Goucher
4,369,919 A    1/1983   Beloev et al.
(Continued)

FOREIGN PATENT DOCUMENTS

EP    2 216 396 A1    8/2010
JP    2006-263419 A   10/2006
(Continued)

OTHER PUBLICATIONS

European Patent Office, "Summons to attend oral proceedings," issued in European Patent Application No. 13 754 261.9, which is a European counterpart of U.S. Appl. No. 16/884,365, dated Oct. 8, 2020, 5 pages.
(Continued)

*Primary Examiner* — Phillip A Gray
(74) *Attorney, Agent, or Firm* — Amster, Rothstein & Ebenstein LLP

(57) ABSTRACT

Provided are a device whereby, during process of a process target such as a cell or the like, localized process of a process
(Continued)

part is possible without inflicting damage due to heat, and rejoining and regeneration may proceed readily subsequent to process, and whereby an injection substance may be introduced efficiently; and a device for generating bubbles containing a plasma.

Through the use of a localized ablation device employing a bubble jetting member having a core formed from a conductive material, a shell part formed from an insulating material, covering the core and including a section extending from the tip of the core, and a space formed between the extended section of the shell part and the tip of the core, a process target can be treated in localized fashion and without inflicting damage. By further providing an outside shell part at the outer periphery of the shell part, bubbles onto which a solution containing an injection substance has been adsorbed can be ejected, and the injection substance can be introduced during localized ablation of the process target. Additionally, by including a pair of electrodes formed from a conducting material, for generating a plasma in an inert gas, a liquid flow passage through which a liquid flows, and a microscopic flow passage for flow of an inert gas, an inert gas containing a plasma, and bubbles of inert gas containing a plasma, the liquid flow passage and the microscopic flow passage connecting at the downstream side from a section in which plasma is generated in the microscopic flow passage, bubbles containing a plasma can be generated, and can maintain a plasma state even in liquid, whereby therapy of biological tissue can be effected with the plasma.

16 Claims, 17 Drawing Sheets

(51) Int. Cl.
| | | |
|---|---|---|
| A61M 5/30 | (2006.01) | |
| C12M 1/42 | (2006.01) | |
| A61B 18/12 | (2006.01) | |
| A61N 1/44 | (2006.01) | |
| A61B 17/3203 | (2006.01) | |
| A61M 5/20 | (2006.01) | |
| A61B 18/00 | (2006.01) | |

(52) U.S. Cl.
CPC ............ *C12M 35/04* (2013.01); *C12N 15/87* (2013.01); *A61B 17/3203* (2013.01); *A61B 2018/00029* (2013.01); *A61B 2018/00577* (2013.01); *A61B 2018/00601* (2013.01); *A61M 5/2066* (2013.01); *A61M 5/3007* (2013.01)

(58) Field of Classification Search
USPC ......................................................... 604/23
See application file for complete search history.

(56) References Cited

U.S. PATENT DOCUMENTS

| 4,855,563 | A | 8/1989 | Beresnev et al. |
| 6,210,404 | B1 | 4/2001 | Shadduck |
| 6,846,306 | B1 | 1/2005 | Haas et al. |
| 6,913,605 | B2 | 7/2005 | Fletcher et al. |
| 6,958,063 | B1 | 10/2005 | Soll et al. |
| 7,589,473 | B2 | 9/2009 | Suslov |
| 2002/0045911 | A1* | 4/2002 | Fletcher ............ A61B 17/3203 606/167 |
| 2002/0183741 | A1 | 12/2002 | Carmel et al. |
| 2003/0125727 | A1 | 7/2003 | Truckai et al. |
| 2007/0029292 | A1 | 2/2007 | Suslov et al. |
| 2010/0317118 | A1 | 12/2010 | Masujima et al. |

FOREIGN PATENT DOCUMENTS

| JP | 2009-500799 A | 1/2009 |
| WO | 1998/012974 A1 | 4/1998 |
| WO | 2000/071038 A1 | 11/2000 |
| WO | 2009/063776 A1 | 5/2009 |

OTHER PUBLICATIONS

Y. Yamanishi et al., "Electric knife for cell surgery: Local ablation by micro-plasma discharge," Micro Electro Mechanical Systems (MEMS), 2012 IEEE 25th International Conference on, IEEE, Jan. 29, 2012 (Jan. 29, 2012), pp. 945-948, XP032137403, DOI:10.1109/MEMSYS.2012.6170342, ISBN:978-1-4673-0324-8.

European Patent Office, "Communication," issued in European Patent Application No. 13 754 261.9, which is a European counterpart of U.S. Appl. No. 14/382,012, dated Mar. 4, 2019, 6 pages.

Korean Intellectual Property Office, "Office Action," issued in Korean Patent Application No. KR 10-2014-7024124, which is a Korean counterpart of U.S. Appl. No. 14/382,012, dated Jan. 29, 2019, 14 pages (9 pages of English Translation of Korean Office Action, 5 pages of Original Korean Office Action).

D. A. Fletcher and D. V. Palanker, "Pulsed liquid microjet for microsurgery," Applied Physics Letters, vol. 78, No. 13, Mar. 26, 2001, pp. 1933-1935, American Institute of Physics.

Korean Intellectual Property Office, "Office Action," issued in KR Patent Application No. KR 10-2017-7005557, which is a Korean counterpart of U.S. Appl. No. 14/382,012, dated Jun. 1, 2018, 11 pages (5 pages of English Translation of Korean Office Action, 6 pages of Original Korean Office Action).

European Patent Office, "Extended European Search Report," issued in European Patent Application No. 13 754 261.9, which is a European counterpart of U.S. Appl. No. 14/382,012, dated Oct. 19, 2015, 9 pages.

Y. Yamanishi, et al., "Transportation of micro-plasma bubble in micro-fluidic chip under atmospheric pressure", IC-PLANTS 2013, The 6th International Conference on PLAsma-Nano Technology & Science, O-03 (2013).

Takahiro Kaji et al., "Nondestructive micropatterning of living animal cells using focused femtosecond laser-induced impulsive force", Applied Physics Letters, vol. 91, 023904 (2007).

Nobuki Kudo et al.. "Sonoporation with microbubbles exposed to pulsed ultrasound", Transactions of Japanese Society for Medical and Biological Engineering, 43 (2), pp. 231-237 (2005).

Daniel Palanker et al., "Anterior capsulotomy with a pulsed-electron avalanche knife", Journal of Cataract & Refractive Surgery, vol. 36, Issue 1, pp. 127-132 (Jan. 2010).

Osamu Sakai et al., "Underwater microdischarge in arranged microbubbles produced by electrolysis in electrolyte solution using fabric-type electrode", Applied Physics Letters, vol. 93, 231501 (2008).

Atsushi Sugimura et al., "Electroporation", Chemistry and Biology, vol. 29. No. 1, pp. 54-60 (1991).

M. Kanemaru et al., "Shingle bubble generated by a pulsed discharge in liquids as a plasma microreactor", Plasma Sources Science and Technology, vol. 20, 034007, p. 7 (2011).

* cited by examiner (a)

(b)

(a)

(b)

BUBBLE JETTING MEMBER AND METHOD FOR PRODUCING SAME, GAS/LIQUID JETTING MEMBER AND METHOD FOR PRODUCING SAME, LOCALIZED ABLATION DEVICE AND LOCALIZED ABLATION METHOD, INJECTION DEVICE AND INJECTION METHOD, PLASMA-BUBBLE JETTING MEMBER, AND THERAPEUTIC DEVICE AND THERAPEUTIC METHOD

CROSS-REFERENCE TO RELATED APPLICATIONS

This application is a Continuation of U.S. patent application Ser. No. 14/382,012, filed on Aug. 29, 2014, which is a U.S. National Stage Entry under 35 U.S.C. § 371 of International Patent Application No. PCT/JP2013/055703 filed on Mar. 1, 2013, which claims the benefit of foreign priority to Japanese Patent Application No. JP 2012-047053 filed on Mar. 2, 2012, and to Japanese Patent Application No. JP 2013-003748 filed on Jan. 11, 2013. The entireties of each of the above-referenced patent applications are incorporated herein by reference.

TECHNICAL FIELD

The present invention relates to a bubble jetting member and a method for producing same, a gas/liquid jetting member and a method for producing same, a localized ablation device and a localized ablation method, an injection device and an injection method, a plasma bubble jetting member, and a therapeutic device and a therapeutic method; and relates in particular to a localized ablation method in which micro/nanobubbles (hereinafter also referred to as "bubbles"), which have been generated by application of high-frequency voltage to a localized ablation device and an injection device while the localized ablation device and the injection device are immersed in a solution, are ejected from the tip of a bubble jetting member or a gas/liquid jetting member, and a process target, such as biological cells or the like, is treated with the ejected bubbles; and an injection method in which, concomitantly with process of biological cells or other process target by a localized ablation method, an injection substance contained in solution adsorbed onto the surfaces of the bubbles is introduced into the process target. The invention also relates to a therapeutic method for therapy of physiological tissue, such as cells or the like, using a plasma generated by application of high-frequency voltage to a therapeutic device.

TECHNICAL BACKGROUND

Advances in biotechnology witnessed in recent years have been accompanied by increasing demand for localized process of cells and the like, involving making a hole in a cell membrane or wall, and removing the nucleus from the cell, or introducing DNA or other nucleic acid substance into the cell. Methods employing a number of localized process techniques (hereinafter sometimes referred to as "localized ablation methods"), such as contact process techniques using a probe, such as an electric scalpel or the like, or non-contact ablation techniques employing lasers or the like, are widely known. In particular, as a contact process technique using an electric scalpel, there has recently been proposed a technique for keeping the cauterization surface to one on the order of several micrometers, thereby minimizing the thermal invasion area and improving the resolution performance (see Non-patent Document 1).

Additionally, in the area of laser process, there have been notable breakthroughs in femtosecond lasers, and techniques for performing cell process (see Non-patent Document 2) and laser process techniques that minimize generation of bubbles in the liquid phase have been recently proposed.

However, in conventional contact process techniques employing a probe such as an electric scalpel, there was a tendency for the target to be burned away due to Joule heat generated by continuous high frequencies, resulting in significant roughness at the incision face and in surrounding tissue being significantly affected by thermal invasion due to heat (Problem 1); and rejoining and regeneration were difficult, due to denaturation of proteins and/or fragmentation of amide bonds (Problem 2). Moreover, with continuous process, adsorption onto the probe of cut proteins and/or adsorption of bubbles generated by heat resulted in the problem of marked degradation of the observation environment at the incision face, making high-resolution process difficult (Problem 3).

In non-contact process techniques employing lasers such as femtosecond lasers and the like as well, tissue surrounding the incision face was affected by localized bombardment with high-density energy, and particularly during process of a target in the liquid phase, generation of bubbles and the like due to heat generated during process made continuous process difficult (Problem 4). Another problem encountered during process of a target in the liquid phase with a laser such as femtosecond laser was difficulty in accessing the process target (Problem 5).

Meanwhile, electroporation, sonoporation techniques employing ultrasound, particle gun methods, and the like are widely known as localized physical injection techniques (injection methods) for introducing nucleic acid substances or the like into cells or the like. Electroporation is a technique in which an electrical pulse is imparted to a cell or the like, thus raising the cell membrane permeability in order to carry out injection; a technique for injection into a thin pliable cell membrane such as lipid bilayer membrane has been proposed (see Non-patent Document 3). In the area of sonoporation techniques employing ultrasound, it has been proposed to bombard bubbles with ultrasound to carry out injection by generating cavitation in a wide range of bubbles (see Non-patent Document 4). Additionally, the particle gun method is a technique involving depositing a substance to be introduced onto a particle, which is then physically shot into the target.

However, in conventional electroporation techniques, depending on the electrical field strength, there are limits as to how much the permeability of the cell membrane can be improved, making it difficult to inject into targets having stiff cell membranes or cell walls, instead of pliable lipid bilayer membranes (Problem 6); and due to restrictions regarding electrode placement and the like, localized injection at the intended site was difficult. Moreover, in sonoporation techniques employing ultrasound, it was difficult to focus the ultrasound, making it difficult to generate localized cavitation of bubbles and increase the resolution (Problem 7).

In injection methods that rely on the particle gun method as well, the problem of low efficiency of introduction, due to separation of the substance deposited on the particle surface occurring when the particle is shot in, was encountered (Problem 8). Additionally, the electroporation, sonoporation, and particle gun methods consume large amounts of substances for injection, making injection of costly substances difficult (Problem 9).

Plasmas are known to be able to contribute to killing malignant cells and healing biological tissue. However, in conventional plasma techniques, it was difficult to bring about a state that would generate a plasma in solution, and while a procedure of first generating a plasma a gas in proximity to the electrodes, and then using the generated plasma to generate bubbles including the plasma in solution, was adopted, the plasma state could not be sustained for an extended period, and it was moreover difficult to move the bubbles while maintaining a plasma state (Problem 10, see Non-patent Documents 5, 6).

PRIOR ART LIST

Non-Patent Documents

Non-patent Document 1: D. Palanker et al., J. Cataract. Surgery, 38, 127-132, (2010)
Non-patent Document 2: T Kaji et al., Applied Physics Letters, 91, 023904, (2007)
Non-patent Document 3: A. Sugimura et al., Kagaku to Seibutsu, 29(1), 54-60, (1991)
Non-patent Document 4: N. Kudo et al., Seitaiikogakkai Shi, 43(2), 231-237, (2005)
Non-patent Document 5: M. Kanemaru et al., Plasma Sources Sci. Technol. 20, 034007, (2011)
Non-patent Document 6: O. Sakai et al., Applied Physics Letters, 93, 231501, (2008)

SUMMARY OF THE INVENTION

Problems to be Solved by the Invention

The present invention is intended to solve the aforedescribed Problems 1 to 10, and as a result of painstaking research, it was discovered that by fabricating a bubble jetting member including a core formed of a conductive material, a shell part formed of an insulating material covering the core and including a section extended from the tip of the core, and a space formed between the extended section of the shell part and the tip of the core, immersing the bubble jetting member in a solution and generating bubbles through the application of high-frequency voltage in the solution, and then continuously ejecting the bubbles into a process target, the treatment target can be cut (localized ablation).

It was also discovered that by additionally furnishing an outside shell part to the outside of the shell part of the bubble jetting member, so that a space is left therebetween, and introducing into the space a solution in which an injection substance has been dissolved and/or dispersed, bubbles having the solution in which the injection substance has been dissolved and/or dispersed adsorbed onto the phase boundary thereof can be generated, and a process target can be cut through continuous ejection of the bubbles against the process target, while at the same time injecting into the process target the injection substance contained in the solution coating the bubbles.

It was further discovered that, by including a pair of electrodes formed of a conductive material, for generating a plasma in an inert gas, a liquid flow passage through which a liquid flows, and a microscopic flow passage for flow of an inert gas, an inert gas containing a plasma, and a liquid containing bubbles of an inert gas containing a plasma, the liquid flow passage and the microscopic flow passage being connected to the downstream side from the section of the microscopic flow passage where plasma is generated; causing an inert gas to flow into the microscopic flow passage, and generating a plasma in the inflowing inert gas by applying a high-frequency electrical pulse to the pair of electrodes; and directing the inert gas containing the plasma to flow into a liquid in the liquid passage which connects to the microscopic flow passage, bubbles containing plasma can be formed through the fluid force of the liquid, and a plasma state can be maintained in the bubbles, even in a liquid.

Specifically, it is an object of the present invention to provide a bubble jetting member and a method for producing same, a gas/liquid jetting member and a method for producing same, a localized ablation device and a localized ablation method, an injection device and an injection method, a plasma bubble jetting member, and a therapeutic device and a therapeutic method.

Means to Solve the Problems

As shown below, the present invention relates to a bubble jetting member and a method for producing same, a gas/liquid jetting member and a method for producing same, a localized ablation device and a localized ablation method, an injection device and an injection method, a plasma bubble jetting member, and a therapeutic device and a therapeutic method.

(1) A bubble jetting member comprising:
a core formed from a conductive material;
a shell part formed from an insulating material, covering the core and including a section extending from a tip of the core; and
a space formed between the extended section of the shell part and the tip of the core.

(2) The bubble jetting member according to (1) above, wherein the extended section of the shell part is tapered.

(3) A gas/liquid jetting member comprising, to the outside of the shell part of the bubble jetting member according to (1) or (2) above, an outside shell part having an axis coaxial with the center axis of the shell part, and formed at a position away from the shell part so that a space is left therebetween.

(4) The gas/liquid jetting member according to (3) above, wherein the section of the outside shell part formed to the outside of the extended section of the shell part is tapered.

(5) The gas/liquid jetting member according to (3) or (4) above, including a solution containing an injection substance, in the space between the shell part and the outside shell part.

(6) The bubble jetting member according to (1) or (2) above, further comprising an electrode part that, together with the core of the bubble jetting member, constitutes a pair of electrodes,
the electrode part being provided as a separate element from the bubble jetting member or on an outer face of the shell part.

(7) The gas/liquid jetting member according to any of (3)-(5) above, further comprising an electrode part that, together with the core of the gas/liquid jetting member, constitutes a pair of electrodes,
the electrode part being provided as a separate element from the gas/liquid jetting member, on an outer face of the shell part, or on an inner face of the outside shell part.

(8) The bubble jetting member according to (1), (2) or (6) above, characterized in that the bubble jetting member is provided with an oscillator.

(9) The gas/liquid jetting member according to (3)-(5) or (7) above, wherein the gas/liquid jetting member is provided with an oscillator.

(10) A localized ablation device employing the bubble jetting member according to (1)-(2), (6), or (8) above, or the gas/liquid jetting member according to (3)-(5), (7), or (9) above.

(11) An injection device employing the gas/liquid jetting member according to (3)-(5), (7), or (9) above.

(12) A method for producing a bubble jetting member, the method comprising: heating and pulling apart from both ends a portion of a hollow tube formed from an insulating material and having a core formed from a conducting material passed through the interior thereof, whereby, due to the difference in viscoelasticity between the insulating material and the conducting material, a shell part is formed in which the insulating material covers the conducting material, and which has a section extending from the tip of the core, and whereby a space is formed between the interior of the extended section of the shell part and the tip of the core.

(13) A method for producing a gas/liquid jetting member, wherein an outside shell part large enough for there to be a space with respect to the shell part of the bubble jetting member according to (12) above is superimposed to the outside of the shell part so as to be coaxial with the center axis thereof.

(14) A localized ablation method, comprising:

immersing the localized ablation device according to (10) above in a solution;

applying a high-frequency electrical pulse to the core of a pair of electrodes which are constituted by the core and the electrode part of the localized ablation device, to eject bubbles from the tip of the bubble jetting member; and processing a process target with the bubbles.

(15) An injection method, comprising:

introducing an injection-substance-containing solution between the shell part and the outside shell part of the injection device according to (11) above;

immersing the injection device in a solution;

applying a high-frequency electrical pulse to the core of a pair of electrodes which are constituted by the core and the electrode part of the injection device, to eject from the tip of the gas/liquid jetting member bubbles onto which the solution containing the injection substance is adsorbed; and introducing the injection substance into a process target, while subjecting the process target to localized ablation with the bubbles.

(16) The injection method according to (15) above, wherein the solution containing the injection substance is introduced between the outside shell part and the shell part by a liquid feed pump, or introduced by capillary action through immersion of a tip part of the gas/liquid jetting member in the solution containing the injection substance.

(17) A plasma bubble jetting member, comprising:

a pair of electrodes formed from a conducting material, and adapted for generating a plasma in an inert gas;

a liquid flow passage through which a liquid flows; and a microscopic flow passage through which flow an inert gas, an inert gas containing a plasma, and a liquid containing bubbles of an inert gas containing a plasma;

the liquid flow passage and the microscopic flow passage connecting at a downstream side from a section in which the plasma is generated in the microscopic flow passage.

(18) The plasma bubble jetting member according to (17) above, wherein the microscopic flow passage includes a plasma reservoir in which the section in which the plasma is generated is made larger than the rest of the microscopic flow passage.

(19) The plasma bubble jetting member according to (18) above, wherein the electrode is of a size at least sufficient to cover the plasma reservoir.

(20) A localized ablation device employing the plasma bubble jetting member according to any of (17)-(19) above.

(21) A therapeutic device employing the plasma bubble jetting member according to any of (17)-(19) above.

(22) A localized ablation method, comprising: causing an inert gas to flow into the microscopic flow passage of the localized ablation device according to (20) above, applying a high-frequency electrical pulse to the pair of electrodes to generate a plasma in the inflowing gas; causing the inert gas containing the plasma to flow into a liquid in the liquid flow channel which connects to the microscopic flow passage, to generate bubbles containing plasma; and processing a process target with the bubbles.

(23) A therapeutic method, comprising: causing an inert gas to flow into the microscopic flow passage of the therapeutic device according to (21) above, applying a high-frequency electrical pulse to the pair of electrodes to generate a plasma in the inflowing gas, causing the inert gas containing the plasma to flow into a liquid in a liquid flow channel which connects to the microscopic flow passage, to generate bubbles containing plasma; and effecting therapy of biological tissue with the bubbles.

Advantageous Effects of the Invention

The space furnished by the tip of the core and the extended section of the shell part acts as a bubble reservoir, whereby a stream of bubbles can be generated continuously in the liquid, and a process target can be cut by the force of collapse of the bubbles when the bubbles collide with the process target. Additionally, due to the microscopic bubble size, damage to the process target can be minimized to the greatest possible extent, thereby solving Problem 1.

Because process of the process target is carried out using bubbles, there is no damage due to thermal invasion, and therefore in cases in which the process target is a biomaterial, denaturation of proteins and the like does not occur, and rejoining and regeneration proceed readily, thereby solving Problem 2.

Because process is carried out using bubbles, there is no damage due to thermal invasion, and therefore no problems such as adsorption of cut proteins onto the electrode probe are encountered, producing the effect of a favorable observation environment at the incision face, thereby solving Problem 3.

The stream of bubbles generated in and ejected from the space are micro/nanoscale in size, and therefore they disappear within a short time through collapse and the like, which has the effect that continuous process is unimpeded by heat generated during process or by generation of the bubbles or the like, producing the effect of making process for an extended period possible, thereby solving Problem 4.

It is possible for a generic manipulator to be easily attached to and detached from the bubble jetting member and the gas/liquid jetting member of the present invention, giving rise to the effect of affording easy access to the process target, thereby solving Problem 5.

By furnishing the outside of the shell part of the bubble jetting member with an outside shell part, in such a way as to have a space in relation to the shell part, and introducing into the space a solution containing an injection substance, simultaneously with ejection of bubbles, the solution between the shell part and the outside shell part is drawn out through fluid force, generating bubbles onto which the solution containing the injection substance is adsorbed, thus making possible a high-output/high-efficiency and rapid process/injection technique, and solving Problem 6.

The bubbles collapse when the bubbles collide with the process target, with process (i.e., ablation) and injection of the process target being carried out simultaneously; and due to the microscopic size of the bubbles, localized injection at high resolution is possible (microscopic scale ablation is possible), thereby solving Problem 7.

Because process and injection by the bubbles are carried out simultaneously, it is possible for various types of injection substances to be encapsulated at the gas-liquid phase boundary; further, the bubbles can be shot in at high speed, at a speed exceeding the speed of diffusion of the injection substance into the surrounding solution, whereby losses due to diffusion of the injection substance into the surrounding solution on the transport pathway around the time of injection are minimal, and efficiency is high, solving Problems 8 and 9.

Situating the electrode part between the shell part and the outside shell part of the gas/liquid jetting member provides a compact, integrated design, making process/injection of targets possible in a wide variety of environments, even in solution.

By providing the bubble jetting member and the gas/liquid jetting member with an oscillator and generating compressional waves, to thereby bring about collapse only of single bubbles at a specific position in the bubble stream at a location where the generated compressional waves overlap, localized injection at the intended site is possible, and resolution can be increased further.

The tip of the bubble jetting member and the gas/liquid jetting member of the present invention has a tapered shape, and therefore when bubbles are ejected, the surrounding solution flows forward along the tapered face, whereby the bubbles can be ejected along the same trajectory even when ejected continuously, so that a predetermined position on the target can be treated.

By employing a localized ablation device and a therapeutic device that include the plasma bubble jetting member of the present invention, even after bubbles containing plasma have been formed through fluid force, the bubbles are maintained in a plasma state within the liquid, thereby solving Problem 10. Further, by including within the microscopic flow passage of the plasma bubble jetting member a plasma reservoir in which the section where the plasma is generated is larger than other sections of the microscopic flow passage, the plasma concentration within the inert gas can be increased, and bubbles containing plasma that can be sustained in a plasma state for extended periods, even in a liquid, can be generated.

DESCRIPTION OF THE EMBODIMENTS

The bubble jetting member and method for producing same, gas/liquid jetting member and method for producing same, localized ablation device and localized ablation method, injection device and injection method, plasma bubble jetting member, and therapeutic device and therapeutic method according to the present invention are described in detail below. In the descriptions of the drawings, like symbols indicate like parts. While the production methods of the present invention and examples of utilization are described in specific terms herein on the basis of presently preferred embodiments for carrying out the present invention, the present invention is not limited to these particular embodiments.

Firstly, in the present invention, "gas/liquid" refers to a bubble having a solution adsorbed onto its phase boundary. A "plasma bubble" refers to a bubble containing a plasma.

First Embodiment

Figure 1:
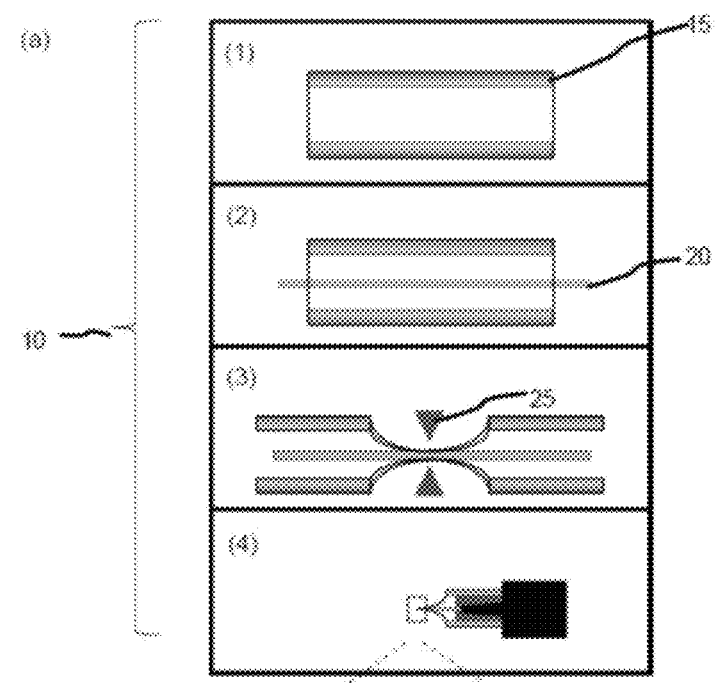
FIG. 1 (a) shows the bubble jetting member production method according to a first embodiment of the present invention, FIG. 1 (b) is a photograph substituting for a drawing, showing an enlarged photograph of a bubble jetting member fabricated by the procedure shown in FIG. 1 (a), and FIG. 1 (c) is a photograph substituting for a drawing, showing a further enlarged photograph.

FIG. 1 (a) shows a method 10 for fabricating a bubble jetting member endowed with a structure having a space at the tip, according to a first embodiment of the present invention. As shown in FIG. 1 (a), the bubble jetting member of the present invention is fabricated by (1) preparing a hollow insulating material 15; (2) inserting a core 20 formed of a conductive material into the hollow insulating material 15; and (3) pulling apart while applying heat 25, whereupon (4) due to a difference in viscoelasticity between the insulating material 15 and the core 20, a shell part 16 which includes a section of the insulating material 15 extended further out from the tip of the core 20 is formed, and a space 30 is formed by the core 20 and the shell part 16, as shown in FIG. 1 (b).

There are no particular limitations as to the insulating material 15 provided it is one that insulates electricity; for example, there can be cited glass, mica, quartz, silicon nitride, silicon oxide, ceramics, alumina, and other such inorganic insulating materials, silicone rubber, ethylene propylene rubber, and other such rubber materials, ethylene vinyl acetate copolymer resins, silane-modified olefin resins, epoxy resins, polyester resins, vinyl chloride resins, acrylic resins, melamine resins, phenolic resins, polyurethane resins, polystyrene resins, fluororesins, silicone resins, polysulfide resins, polyamide resins, polyimide resins, polyethylene, polypropylene, cellulose resins, UV-curing resins, and other such insulating resins.

There are no particular limitations as to the conducting material forming the core 20, provided it is one that conducts electricity; for example, there can be cited gold, silver, copper, aluminum, and the like, as well as alloys to which small amounts of tin, magnesium, chromium, nickel, zirconium, iron, silicon, or the like, have been added. As described above, the space 30 is formed by the tip of the core 20 and a section of the insulating material 15 extended further out from the tip of the core 20, and therefore any combination of appropriate materials such that the viscoelasticity of the insulating material 15 is greater than the viscoelasticity of the core 20 is acceptable, for example, a combination of glass as the insulating material 15, and copper as the core 20.

FIG. 1 (b) is a photograph of a bubble jetting member fabricated by inserting copper wire 30 μm in diameter into a glass hollow tube (made by Drummond Corp., outside diameter 1.37 mm, inside diameter 0.93 mm), and heating while pulling apart using a glass puller (P-1000IVF made by Sutter).

FIG. 1 (c) is a further enlarged photograph of FIG. 1 (b). As will be discussed below, when high-frequency voltage is applied to the bubble jetting member of the present invention, bubbles are continuously ejected from the tip of the bubble jetting member, and during this time, first, bubbles of a size approximating a diameter (D) are generated in the space 30, whereupon the bubbles are ejected in a burst from the tip of the bubble jetting member. Consequently, it is necessary for the depth (L) of the space 30 to be of at least a size that allows bubbles to be generated within the space 30; in preferred practice L/D is equal to at least 1. While there is no particular upper limit as to L/D provided that bubbles can be continuously jetted, the tip of the bubble jetting member is exceedingly fine and susceptible to breakage, and therefore from the standpoint of convenience in handling and the like, L/D is preferably 1-4, more preferably 1-3, still more preferably 1-2, and especially preferably 1-1.5. With consideration to the relationship of temperature and viscosity of the material during production, L/D can be adjusted by changing the speed of pulling apart, and the temperature during heating. By adjusting the diameter of the opening at the tip of the bubble jetting member, the size of the bubbles ejected therefrom can be adjusted. As stated above, the diameter of the opening can be adjusted by changing the speed of pulling apart, and the temperature during heating.

The bubble jetting member production method is not limited to the aforedescribed example, and production by, for example, providing the tip of the core 20 with a member of a photoresist, thermosetting resin, or the like, then providing about the circumference of the core 20 an insulating material such as silicon nitride, silicon oxide, or the like by a sputtering process, and thereafter removing the photoresist, thermosetting resin, or the like, would also be acceptable. Alternatively, the tip of the core 20 may be provided with a photoresist, thermosetting resin, or the like of tapered shape, to impart a tapered shape to the shell part subsequent to sputtering. In the case of producing the bubble jetting member by a sputtering process, appropriate adjustments may be made to the length of the bubble jetting member provided to the tip of the core 20, to adjust the aforementioned L/D.

Figure 2:
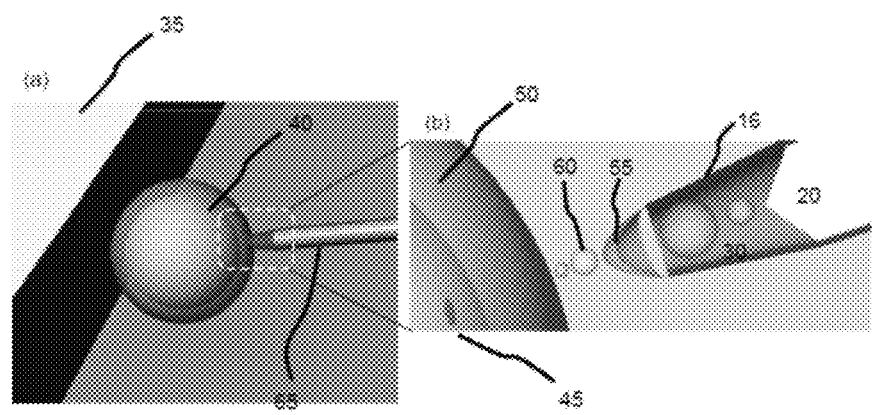
FIG. 2 (a) is a diagram describing a localized ablation method employing the bubble jetting member of the present invention, and FIG. 2 (b) is a descriptive diagram in which the section indicated by broken lines in FIG. 2 (a) has been further enlarged.

FIG. 2 is a diagram describing a localized ablation method employing the bubble jetting member of the present invention. In the example shown in FIG. 2 (a), a bovine egg 40 serving as the process target is placed between an active electrode 65 (the core 20 of the bubble jetting member) and a counter electrode 35 separate from the bubble jetting member. FIG. 2 (b) is a descriptive diagram further enlarging the broken line section in FIG. 2 (a), with bubbles accumulating in the space 30 at the tip of the bubble jetting member, and a bubble 60 ejected from the tip of the bubble jetting member colliding against the zona pellucida 50 of the bovine egg 40, opening up a hole so that the nucleus 45 of the bovine egg can be removed.

Figure 3:
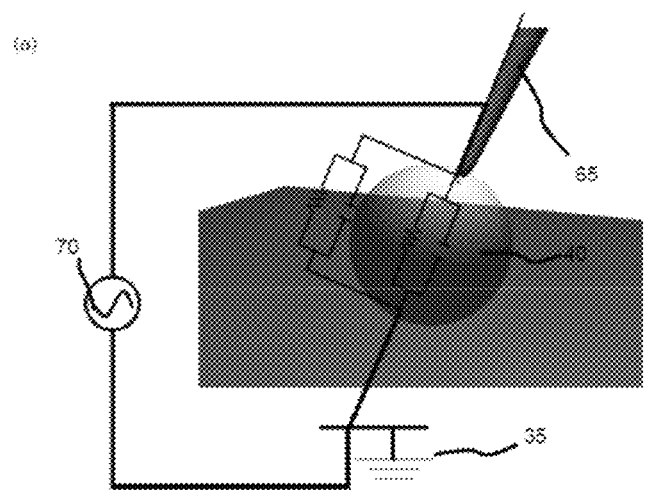
FIG. 3 (a) shows an equivalent electrical circuit diagram of the environs of a biomaterial in a localized ablation device employing the bubble jetting member of the present invention, and FIG. 3 (b) shows a circuit diagram for generating output adapted to a minute process target, in which non-inductive resistance has been introduced into a conventional electric scalpel circuit.
Figure 3:
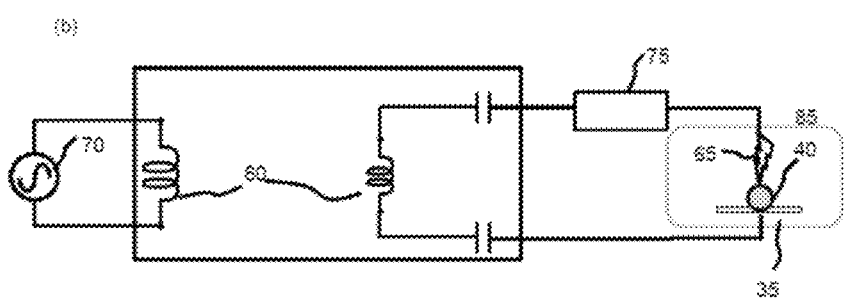

FIG. 3 (a) shows an electrical circuit diagram of a localized ablation device employing the bubble jetting member of the present invention. By immersing the bubble jetting member in a solution, a circuit is formed by the active electrode 65 (the core 20) and the counter electrode 35, and by applying voltage using an ordinary commercial AC power supply unit 70, the bubble jetting member can be employed as a localized ablation device. The circuit shown in FIG. 3 (a) can be produced simply by incorporating non-inductive resistance 75 into a conventional electric scalpel circuit as shown in FIG. 3 (b), and setting it to an output configuration for minute target use. There are no particular limitations as to the solution provided it can conduct electricity; in cases in which the process target is a cell or the like, because electrolytes contained in the culture broth have conducting action, the broth can be employed without further modification. Any desired cell can be selected as a cell to serve as the process target in the present invention, with no particular limitation as to cell type. As specific examples, there can be cited cells isolated from human or non-human animal tissue, such as stem cells, skin cells, mucosal cells, liver cells, pancreatic islet cells, nerve cell, cartilage cells, endothelial cells, epidermal cells, bone cells, muscle cells, egg cells, and the like, as well as plant cells, insect cells, or microbial cells of coliform bacteria, yeasts, fungi, and the like. In the present invention, "process" refers to making a hole in cell or the like by jetting bubbles against the cell, to make an incision in a portion of the cell.

Figure 4:
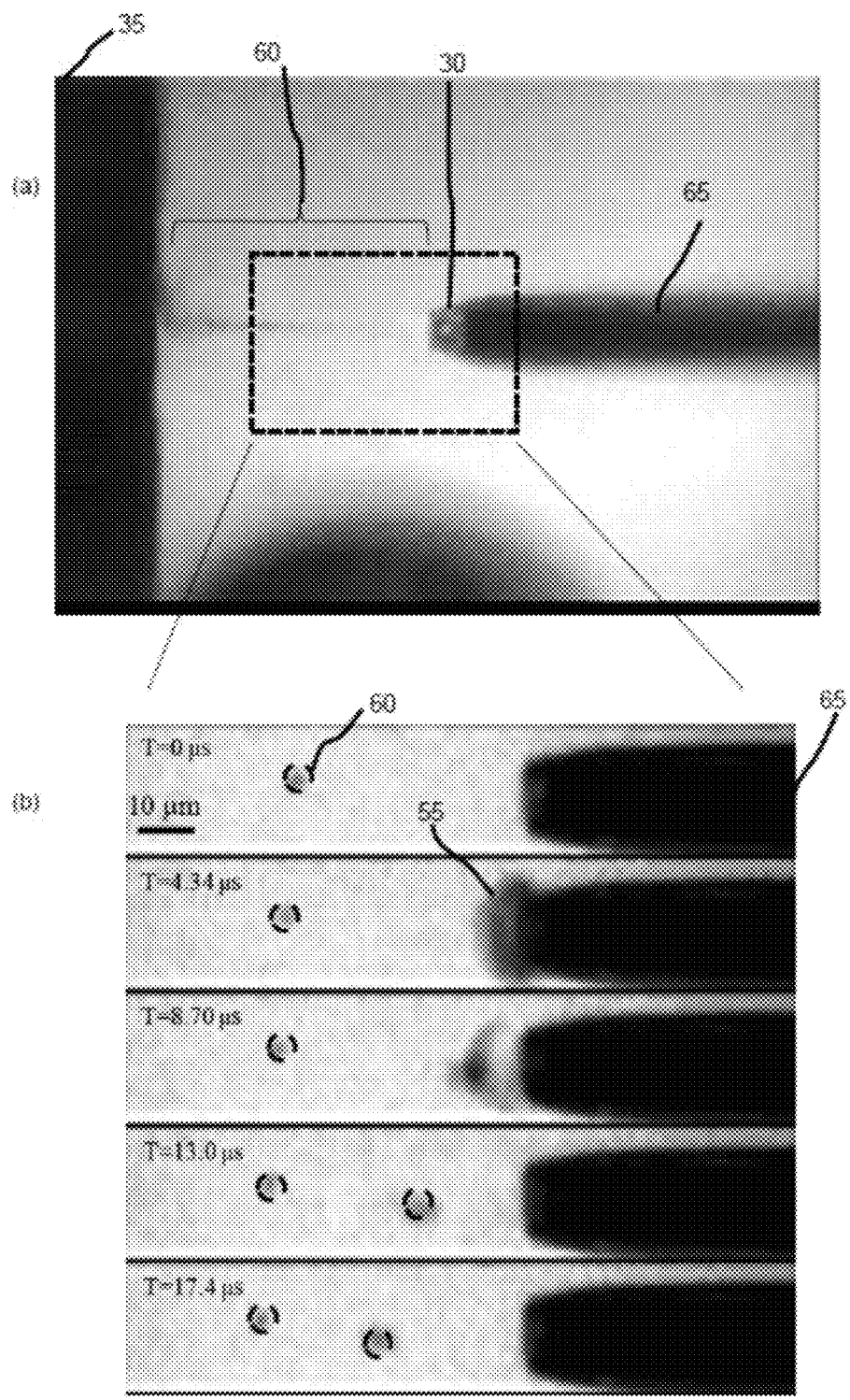
FIG. 4 (a) is a photograph substituting for a drawing, showing generation of a directional microscopic bubble stream, from the tip of a localized ablation device employing the bubble jetting member of the present invention, and FIG. 4 (b) shows photographs substituting for a drawing, showing further enlarged moment-by-moment photographs of the section indicated by broken lines in FIG. 4 (a)

FIG. 4 (a) is a photograph showing generation of a directional microscopic bubble stream, from the tip of the bubble jetting member of the localized ablation device of the present invention. The localized ablation device of the present invention was fabricated by incorporating the bubble jetting member shown in FIG. 1 into the medical electric scalpel shown in FIG. 3 (Hyfrecator 2000 made by ConMed Inc.). The output frequency was 450 kHz, the sampling frequency for impedance matching was 450 kHz, and feedback was carried out at 3.5 kHz. FIG. 4 (b) shows further enlarged photographs of the section indicated by the broken lines in FIG. 4 (a), in which a directional microscopic bubble stream 60 is generated in the form of a stream, from the space 30 in which bubbles have accumulated at the tip of the bubble jetting member. Because the ejected bubbles are directional, it is possible to limit the cell process area. As shown in FIGS. 4 (a) and (b), bubbles were ejected at regular intervals; the reason for this is thought to be that since a medical electrical scalpel typically applies high-frequency electric pulses, they correspond to the intervals at which pulses are applied.

Figure 5:
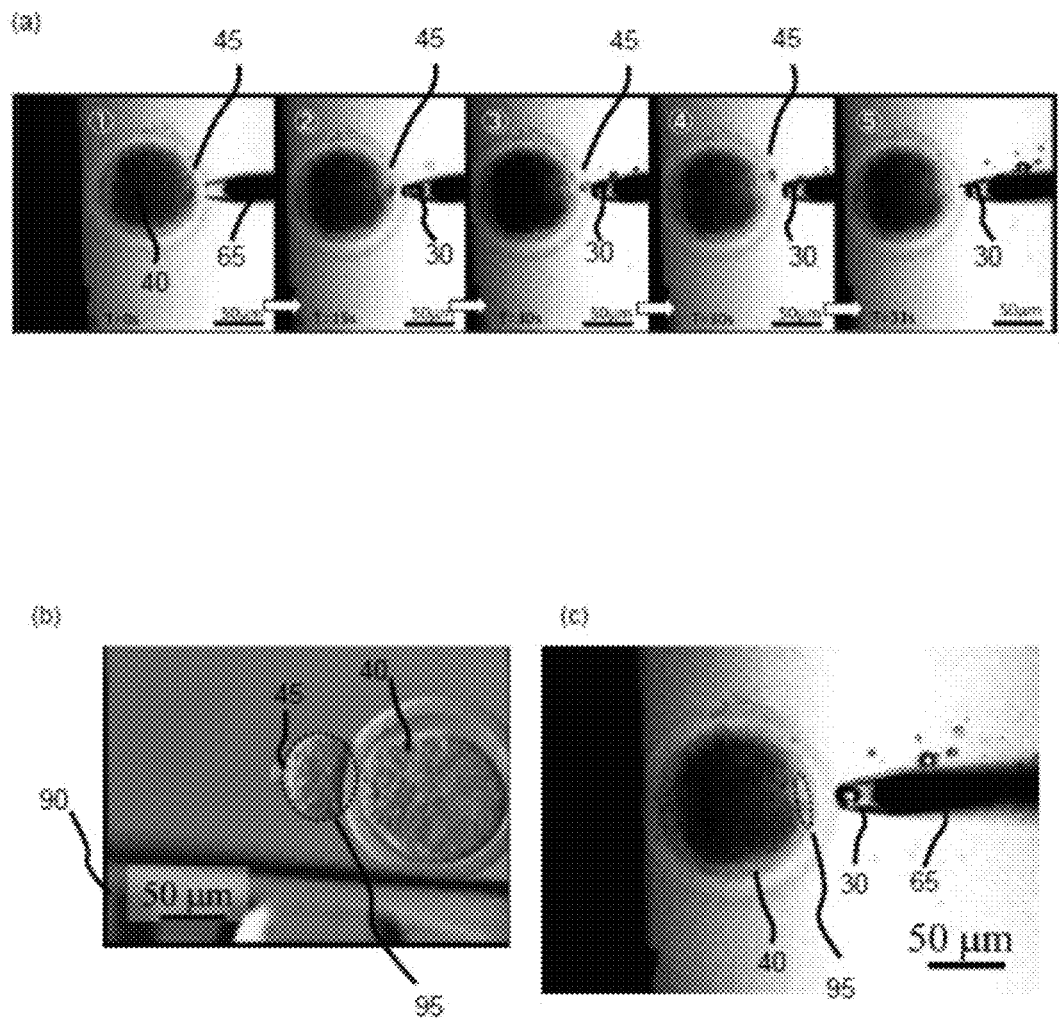
FIG. 5 (a) shows photographs substituting for a drawing, showing a successful experiment to enucleate an egg, employing a localized ablation device employing the bubble jetting member of the present invention, FIG. 5 (b) is a photograph substituting for a drawing, showing an area enucleated by a microscopic procedure using a conventional glass capillary, and FIG. 5 (c) is a photograph substituting for a drawing, showing an area enucleated using the localized ablation device of the present invention, compared with FIG. 5 (b)

FIG. 5 (a) shows a successful experiment to enucleate a bovine egg 40 with a localized ablation device employing the bubble jetting member of the present invention. The applied voltage conditions of the localized ablation device are the same as above. As will be understood from FIG. 5 (a), the nucleus 45 of the bovine egg 40 could be removed out from the cell by ejecting bubbles. FIG. 5 (b) shows a removal area 95 where the nucleus 45 was removed from the bovine egg 40 by a microscopic procedure using a conventional glass capillary 90, while FIG. 5 (c) shows a removal area 95 where the nucleus was removed from the bovine egg 40 with a localized ablation device employing the bubble jetting member of the present invention. As may be understood from FIGS. 5 (b) and (c), as compared with the case of enucleation using the conventional glass capillary, when enucleation was performed with the localized ablation device employing the bubble jetting member of the present invention, damage to the bovine cell 40 or other process target was reduced.

Second Embodiment

A second embodiment of the present invention will be described below, while referring to the drawings. The reference numerals in the drawing are the same as those in the first embodiment.

Figure 6:
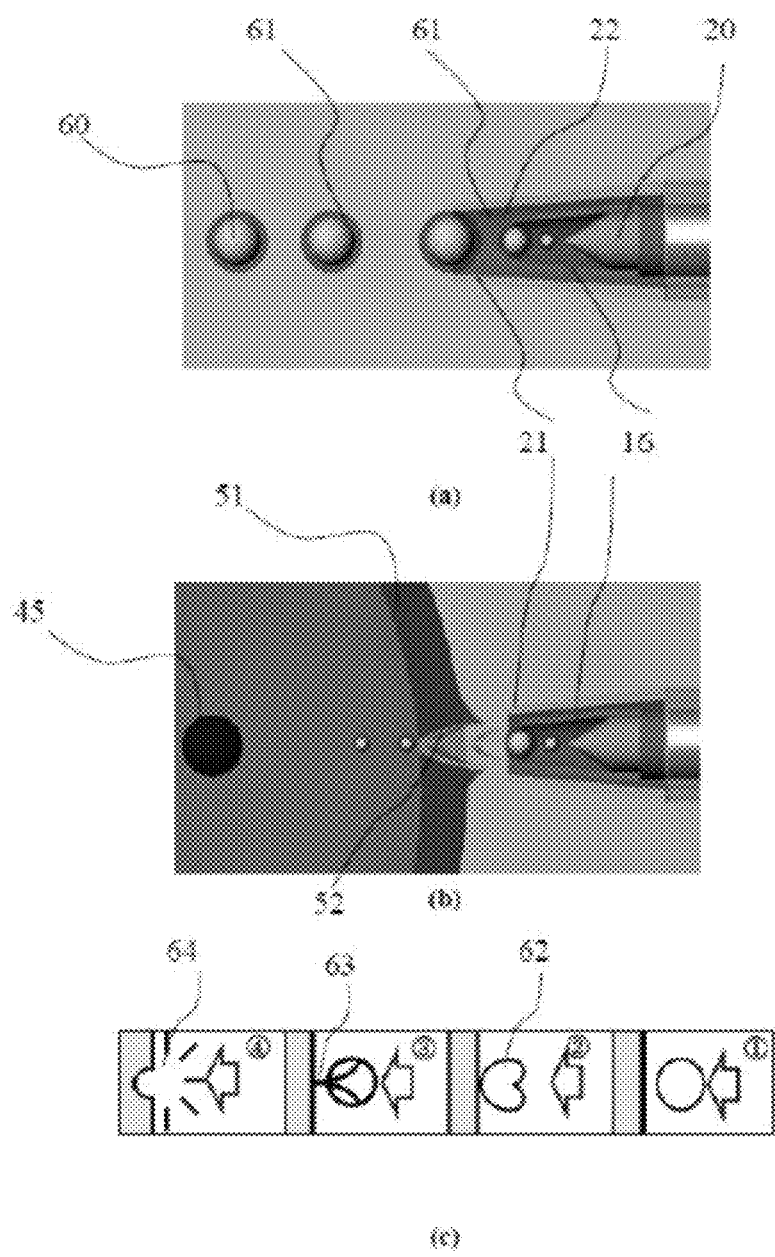
FIG. 6 (a) is a model diagram showing a simplification of a localized ablation method and an injection method employing the gas/liquid jetting member of the present invention, FIG. 6 (b) is a model diagram showing injection through rupture of a cell membrane by an ejected bubble, and FIG. 6 (c) is a model diagram representing bubble cavitation in a step-by-step (moment-by-moment) fashion.

FIG. 6 (a) is a model diagram showing a simplification of a localized ablation method and an injection method employing the gas/liquid jetting member of the present invention. The gas/liquid jetting member of the second embodiment has an outside shell part 21 formed to the outside of the shell part 16 of the bubble jetting member of the first embodiment, at a location away from the shell part 16; by introducing a solution 61 containing an injection substance in advance into a space 22 formed by the shell part 16 and the outside shell part 21, a bubble onto which the solution 61 containing the injection substance is adsorbed can be ejected from the tip of the gas/liquid jetting member. FIG. 6 (b) is a diagram showing injection through rupture of a cell membrane by an ejected bubble 60; the impact of collapse (cavitation) of the ejected bubble (60) makes a hole in the cell membrane 51, so that the injection substance can reach the cell interior. FIG. 6 (c) is a diagram representing cavitation of the bubble 60 in a step-by-step fashion; as the bubble advances at high speed, a pressure disequilibrium arises, causing the spherical shape 62 to deform, and during collapse of the bubble, there is generated a high-output micro-jet 63 at high resolution, whereupon the front face of this micro-jet 63 in the direction of advance of an ejection phase boundary 52 protrudes out, and through high-pressure gas, a hole 64 is made in the process target due to the force of the micro-jet 63.

The material for forming the outside shell part 21 may be the same material as the shell part 16. The injection substance may be a gas, a solid, or a liquid, with no particular limitations provided it can be dissolved and/or dispersed in solution; as gases, there can be cited air, nitrogen, helium, carbon dioxide, carbon monoxide, argon, oxygen and the like; as solids, DNA, RNA, proteins, amino acids, inorganic matter, and the like; and as liquids, drug solutions, amino acid solutions, and the like. Physiological saline, culture media, and the like may be cited as examples of solutions in which the injection substance is dissolved and/or dispersed.

Figure 7:
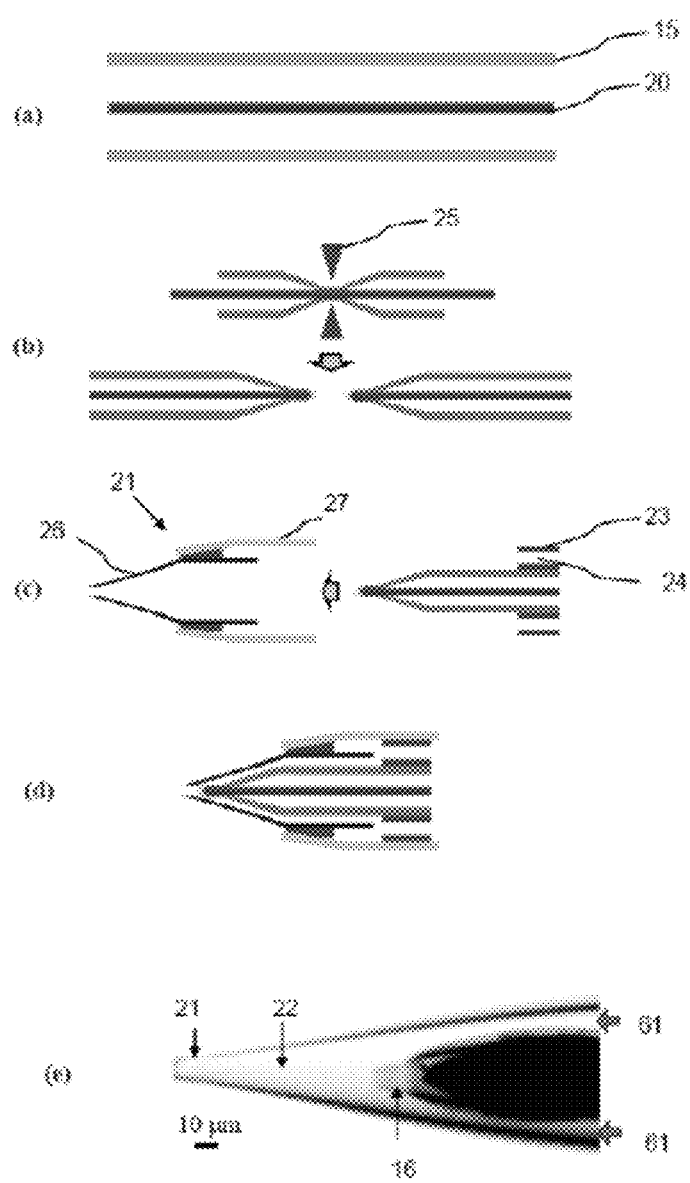
FIG. 7 (a) is a diagram showing a simplification of a gas/liquid jetting member production method of a second embodiment, and FIG. 7 (e) is a photograph substituting for a drawing, showing a photograph of the tip section of the gas/liquid jetting member of the second embodiment.

FIG. 7 (a) is a diagram showing a simplification of a gas/liquid jetting member production method of a second embodiment. After producing a bubble jetting member by the same procedure as in steps (1) to (4) in the first embodiment (these steps correspond to FIG. 7 (a) and (b)), (c) a coaxial positioning washer 23, fabricated by a method such as a photolithography/3D optical shaping process or the like using a polymer film, rubber washer, or polydimethyl siloxane (PDMS) is fitted onto the bubble jetting member of the first embodiment, whereupon the outside shell part 21, which has been fabricated by pulling apart a glass tube, plastic tube, or the like by heat, is slid onto the outside of the washer 23, whereby (d) the gas/liquid jetting member of the second embodiment can be produced. As will be discussed below, in order to be able to feed the solution 61 containing the injection substance by a pump, not illustrated, it is preferable for the washer 23 to include a hole 24. The outside shell part 21 may be one fabricated by pulling apart a glass tube or plastic tube in the aforedescribed manner, and fitted directly onto the washer 23; or, as shown in (c), the outside shell part 21 may be fabricated by adhesive bonding of a guide 27 fabricated from plastic or the like (for example, an Eppendorf tube (an Ibis (R) pipette tip IN122-503Y) about pulled-apart glass 26 or the like, and the guide 27 section then fitted onto the washer 23. The outside shell part 21 may be provided with multiple layers, so that solutions containing different types of injection substances can be introduced between the layers. Additionally, while not illustrated in the drawings, in the aforedescribed step (c), a conductive counter electrode of copper or the like may be arranged on the outside face of the shell part 16 or the inside face of the outside shell part 21. In cases in which the counter electrode is provided to the gas/liquid jetting member, as it is sufficient for the counter electrode to be able to form a circuit with the core 20, there is no particular limitation as to the location, provided it comes in contact with the solution 61 containing the injection substance, which fills the space 22. The counter electrode can also be provided as a separate element from the gas/liquid jetting member. FIG. 7 (e) is a photograph of the tip section of a gas/liquid jetting member fabricated by the above procedure. In specific terms, the outside shell part 21 was fabricated by heating a glass hollow tube (made by Drummond Corp., outside diameter 2.03 mm, inside diameter 1.63 mm) one size larger than the glass hollow tube employed to fabricate the aforedescribed bubble jetting member, doing so while pulling it apart using a glass puller (P-1000IVF made by Sutter). A washer fabricated by lamination of polymer film, not illustrated, is then fitted onto the bubble jetting member, and the fabricated outside shell part 21 is slipped about the outside of the washer. To the inside of the fabricated outside shell part 21 is provided a copper electrode of cuboid shape, not illustrated. Using a pump, not illustrated, the solution 61 containing the injection substance is fed into the space 22 formed between the shell part 16 and the outside shell part 21.

Figure 8:
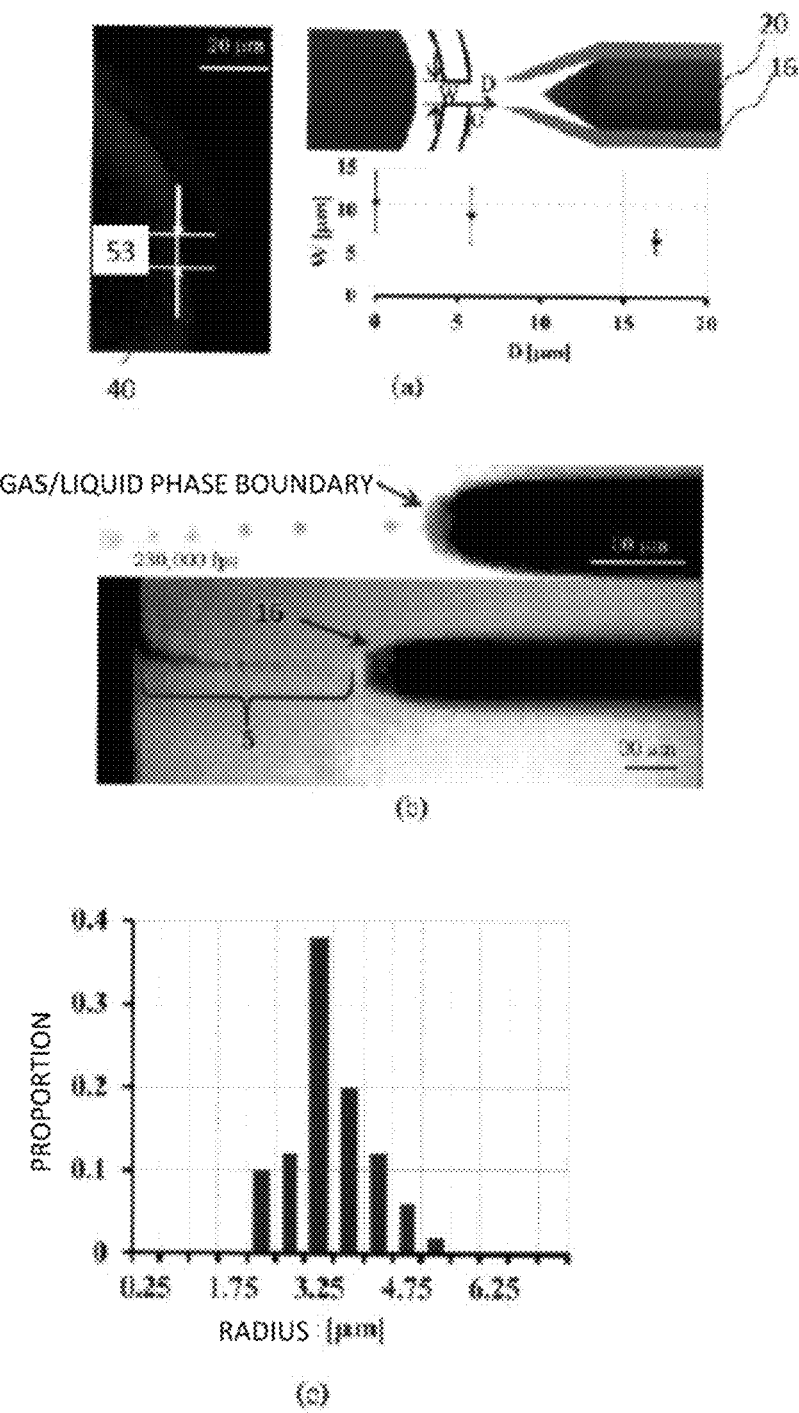
FIG. 8 (a) is a diagram showing the relationship of process width during collapse of a generated microbubble, and distance between the process target and the tip of the bubble jetting member, and a confocal microscopic photograph showing process accuracy, FIG. 8 (b) is a photograph substituting for a drawing, showing a microbubble stream of directional monodispersed bubbles generated during application of a high-frequency electrical pulse, and FIG. 8 (c) shows a size distribution of bubbles in the generated microbubble stream.

FIG. 8 (a) shows the relationship of distance between the process target and the tip of the bubble jetting member, and the process width during collapse of a microbubble generated by a localized ablation device employing the bubble jetting member of the first embodiment (having a tip diameter of approximately 10 µm); and a confocal microscopic photograph showing process accuracy. FIG. 8 (b) shows a microbubble stream 5 of directional monodispersed bubbles generated during application of a high-frequency electrical pulse. FIG. 8 (c) shows the size distribution of bubbles in the generated microbubble stream. As shown in FIG. 8 (a), as the distance between the tip of the bubble jetting member and the process target (the bovine egg 40) at the time of collapse of a bubble increased, the process width 53 became smaller, and the resolution was on the order of a process width of several microns. As shown in (c), the size of a bubble generated in a case in which the shell part 16 of the bubble jetting member has an opening diameter of 10 µm exhibited the greatest distribution at a radius of approximately 3.25 µm.

Figure 9:
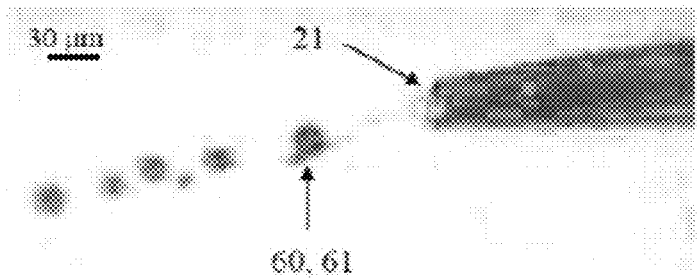
FIG. 9 (a) is a photograph substituting for a drawing, showing ejection of a bubble on which a methylene blue solution has been adsorbed onto the circumference of the bubble, employing the gas/liquid jetting member of the second embodiment, and FIG. 9 (b) is a photograph substituting for a drawing, showing a time series of conditions when carrying out localized ablation and injection of a cell, using fluorescent beads as an injection substance.
Figure 9:
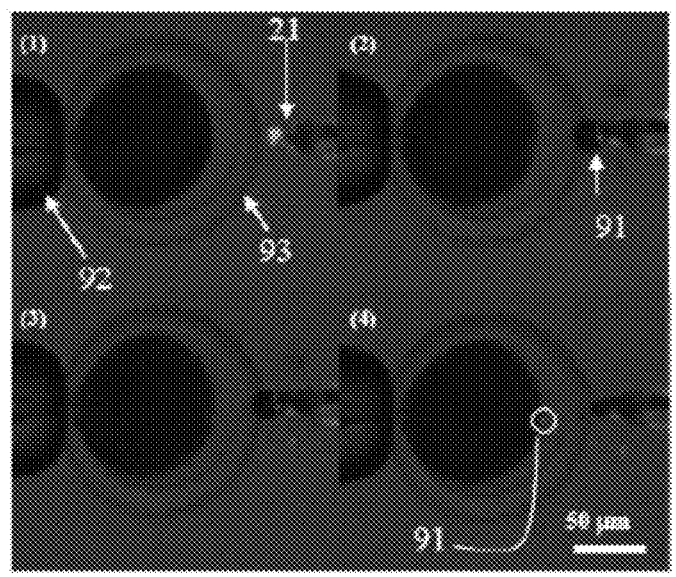

FIG. 9 is a photograph showing ejection of a bubble 60 onto the circumference of which has been adsorbed a solution containing an injection substance, when employing the gas/liquid jetting member of the second embodiment of the present invention. As the solution 61 containing the injection substance, a methylene blue solution of powdered methylene blue dissolved in TCM199 medium to a concentration of 10 mg/mL was used, and was introduced by capillary action into the space 22 at the tip of the gas/liquid jetting member produced in the second embodiment. Next, the gas/liquid jetting member into which the methylene blue solution had been introduced was incorporated into the same medical electric scalpel as in the first embodiment (Hyfrecator 2000 made by ConMed Inc.); the output frequency was 450 kHz, the sampling frequency for impedance matching was 450 kHz, and feedback was carried out at 3.5 kHz. As shown in FIG. 9 (a), the bubble stream ejected from the tip of the gas/liquid jetting member was entirely blue. From this, it was confirmed that the bubble 60 was covered by the methylene blue solution 61. From the fact that the ejected bubble 60 retained its blue color during travel through the solution, it was confirmed that the methylene blue solution 61 adsorbed onto the bubble phase boundary did not diffuse into the surrounding solution, but instead remained adsorbed on the bubble 60 during travel. Consequently, by dissolving and/or dispersing an injection substance, such as a nucleic acid, protein, or the like, into a solution adsorbed onto the phase boundary of a bubble, the injection substance can be introduced into a process target such as a cell or the like, in the course of localized ablation. FIG. 9 (b) contains photographs showing a time series of conditions when carrying out localized ablation and injection of a cell, using fluorescent beads 91 as the injection substance. Using a bovine egg as the cell employed as the process target, 10 mg of the fluorescent beads 91 (Fluoro-Max made by Thermo Scientific Co., diameter 2.1 µm) were dispersed in 1 mL of TCM199 medium, to prepare the injection substance. The bovine egg was immobilized with a suction pipette 92, and localized ablation and injection were carried out by the same procedure as in (a) above, as a result of which a phenomenon whereby the fluorescent beads 91 were introduced into the cell through the egg cell wall 93 was confirmed.

Figure 10:
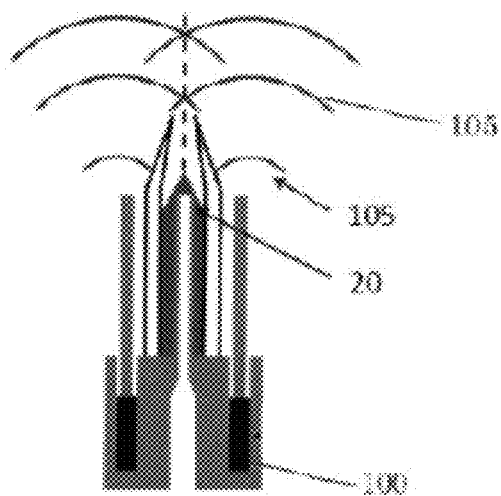
FIG. 10 (a) is a model diagram showing generation of dilational waves by an oscillator installed in the bubble jetting member, and FIG. 10 (b) is a model diagram showing active compression of only a single one in a bubble stream by overlapping dilational waves.
Figure 10:
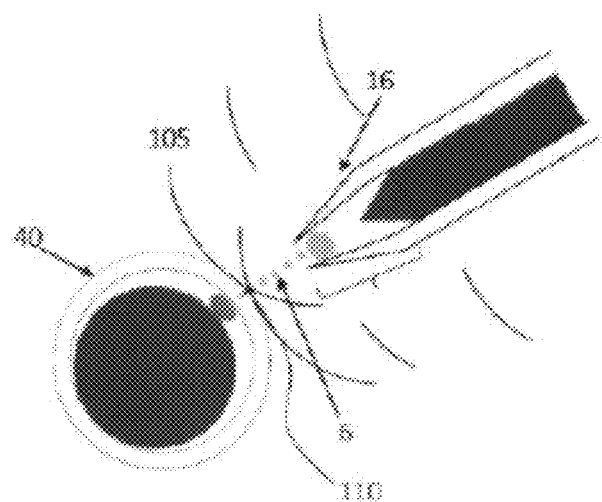

FIG. 10 (a) is a model diagram showing generation of dilational waves 105 by an oscillator installed in the bubble jetting member, and FIG. 10 (b) is a model diagram showing active compression of only a single one in a bubble stream by overlapping dilational waves 105. Oscillators 100 installed outside the bubble jetting member generate compressional waves 105, and in an overlapping part 110 of the compressional waves, it is possible to collapse only a single one within a bubble stream, to carry out highly accurate process. As the oscillators 100, there could be employed any oscillator that is typically easily procurable, such as piezo elements, crystals, or the like, arranging at least two oscillators to the outside of the bubble jetting member, connecting the respective oscillators to an external power supply, and applying synced pulse voltage. The oscillators may of course be installed in the gas/liquid jetting member also.

Third Embodiment

Figure 11:
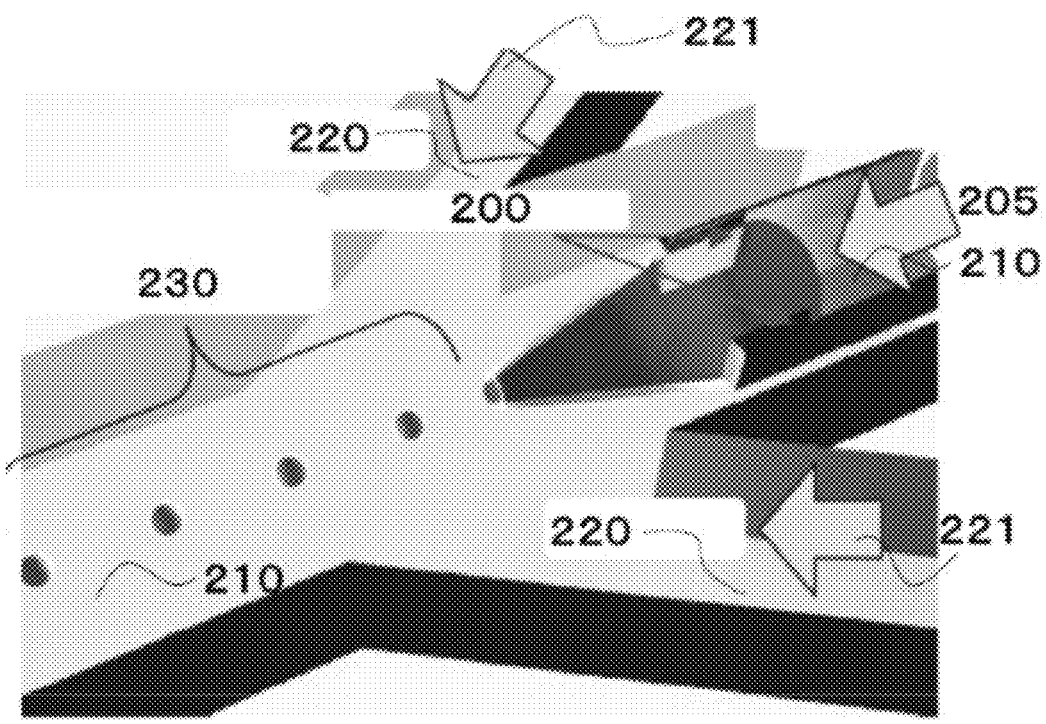
FIG. 11 is a diagram showing a simplification of a plasma bubble jetting member according to a third embodiment of the present invention.

A third embodiment of the present invention will be described below while referring to the drawings. FIG. 11 shows a simplification of a plasma bubble jetting member according to a third embodiment of the present invention.

As shown in FIG. 11, at a minimum, the plasma bubble jetting member includes: a pair of electrodes 200 formed of a conductive material on a substrate; a microscopic flow passage (micro-flow passage) 210 for flowing a liquid containing bubbles 230 containing an inert gas 205 and a plasma; and a liquid flow passage 220 connecting to the microscopic flow passage 210, to the downstream side from the section of the microscopic flow passage 210 where plasma is generated. By applying a high-frequency electrical pulse to the electrodes 200, a plasma is generated in the inert gas 205 inflowed to the microscopic flow passage by a pump, not illustrated, whereupon the inert gas containing the plasma flows to the downstream side, where it is severed by fluid force during intersection with a liquid 221 flowing through the liquid flow passage 220, whereby bubbles 230 of inert gas containing plasma can be ejected. The angle of the section in which the microscopic flow passage 210 and the liquid flow passage 220 connect is not particularly limited, and can be any angle such that the inert gas 205 is severed by fluid force during intersection with a liquid 221 as described above. In the event that the angle formed by the flow direction of the inert gas 205 and the flow direction of the liquid 221 is parallel, no bubbles will be generated, whereas if it exceeds 90 degrees, the inert gas will be pushed back by the liquid 221. Consequently, the angle of the section in which the microscopic flow passage 210 and the liquid flow passage 220 connect must be at least greater than 0 degrees but not more than 90 degrees, preferably 20-90 degrees, and more preferably 45-90 degrees. While bubbles can be generated by fluid force as long as at least one fluid flow channel 220 is provided, in order to achieve uniform bubble size, it is preferable to form two or more fluid flow channels 220, in such a way that the fluid force acting on the inflowing inert gas is homogeneous. In cases in which three or more fluid flow channels 220 are formed, these may be arranged three-dimensionally.

The materials cited as the aforementioned insulating material 15 can be employed in the substrate of the plasma bubble jetting member as well. Materials similar to the aforementioned conductive material 20 can be employed as the conductive material for forming the electrodes 200. As the inert gas 205, there may be cited helium, nitrogen, neon, argon, and the like. There are no particular limitations as to the liquid 221 provided that it is one in which bubbles can form; water, culture broth, and the like can be cited, for example. A reagent or the like may be mixed into the liquid, in order to confirm the condition of plasma generation.

Figure 12:
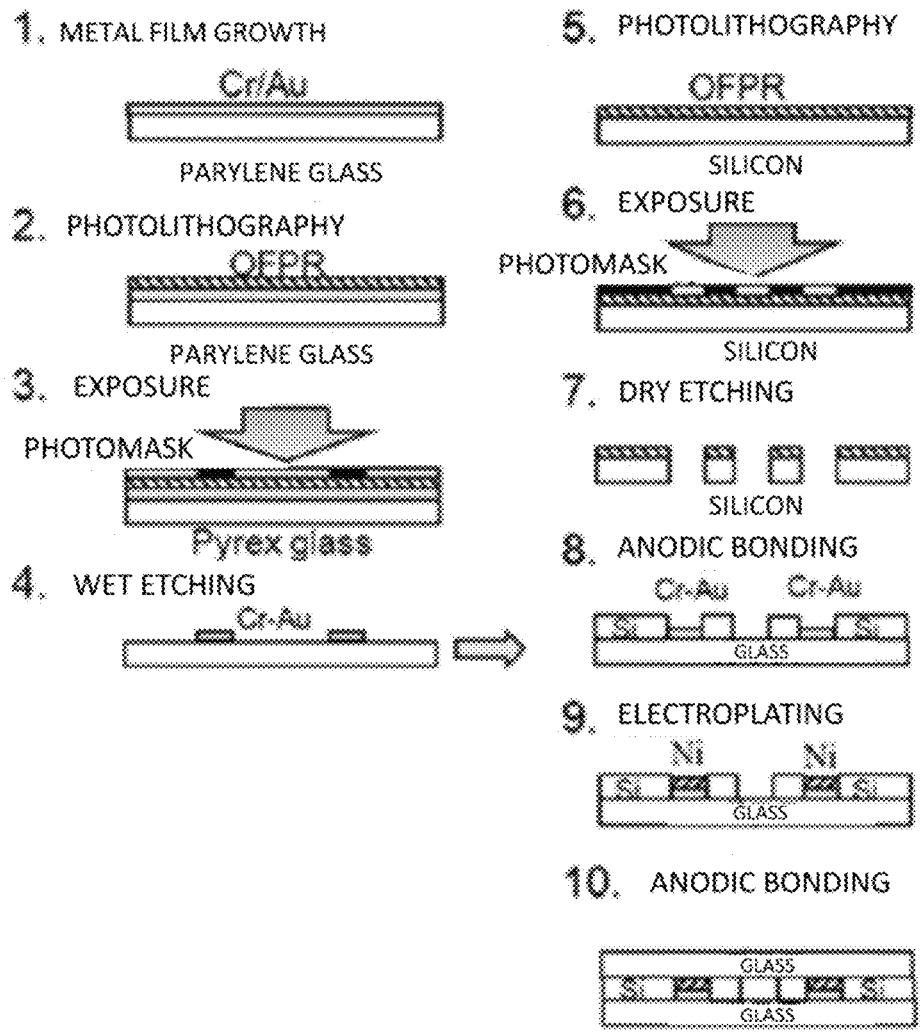
FIG. 12 is a diagram showing a fabrication method for the plasma bubble jetting member according to a third embodiment of the present invention.

FIG. 12 is a diagram showing a procedure for fabricating the plasma bubble jetting member shown in FIG. 11. (1) A thin metal film of chromium and gold was grown on Parylene glass 500 μm in thickness, and (2) OFPR (Tokyo Ohka Kogyo Co. Ltd.), a positive resist, was spun-coated thereon. (3) Thereafter, exposure with g-rays (436 nm) was carried out through a photomask, followed by development with NMD-3 (Tokyo Ohka Kogyo Co. Ltd., a 2.38 wt % tetramethylammmonium hydroxide aqueous solution). (4) Next, wet etching was carried out with an etchant for chromium and gold (Nihon Kagaku Sangyo Co. Ltd.), producing a substrate bottom having electrodes of a thin metal film of chromium and gold. (5) Meanwhile, for the substrate that included the liquid flow passage 220, a silicon substrate 150 μm in thickness was spun coated with OFPR (Tokyo Ohka Kogyo Co. Ltd.). (6) Thereafter, exposure with g-rays (436 nm) was carried out through a photomask, followed by development with NMD-3, and then silicon etching was carried out with $SF_6$ gas and $C_4F_8$ gas by a (7) DRIE (dry etching) process. (8) Thereafter, the fabricated substrate including the liquid flow passage 220, and the substrate bottom fabricated by the procedure of the aforementioned steps (1) to (4), were bonded by anodic bonding, after which (9) an electroplating process was carried out to deposit nickel electrodes to a depth of 150 μm over the electrodes of the thin metal film of chromium and gold on the substrate bottom. (10) Further, Parylene glass 500 μm in thickness was bonded by anodic bonding as a top substrate onto the substrate.

Figure 13:
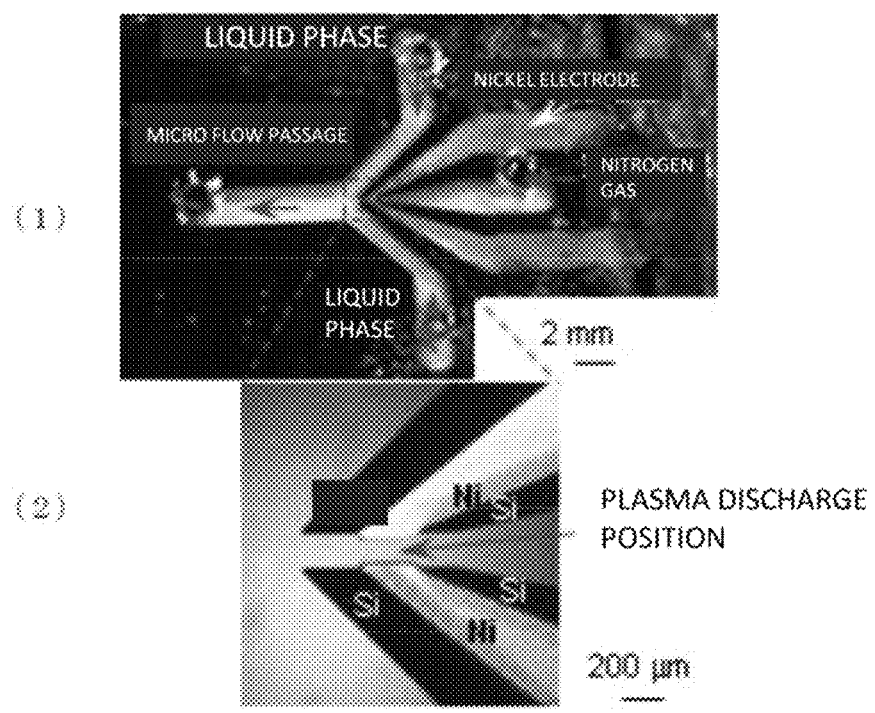
FIG. 13 (1) is an optical microscopic photograph of a plasma bubble jetting member fabricated in accordance with the procedure of FIG. 12, and FIG. 13 (2) is a model diagram in which the broken line section in (1) is enlarged.

FIG. 13 (1) is an optical microscopic photograph of a plasma bubble jetting member fabricated in accordance with the procedure of FIG. 12, and FIG. 13 (2) is a model diagram in which the broken line section in FIG. 13 (1) is enlarged.

Fourth Embodiment

Figure 14:
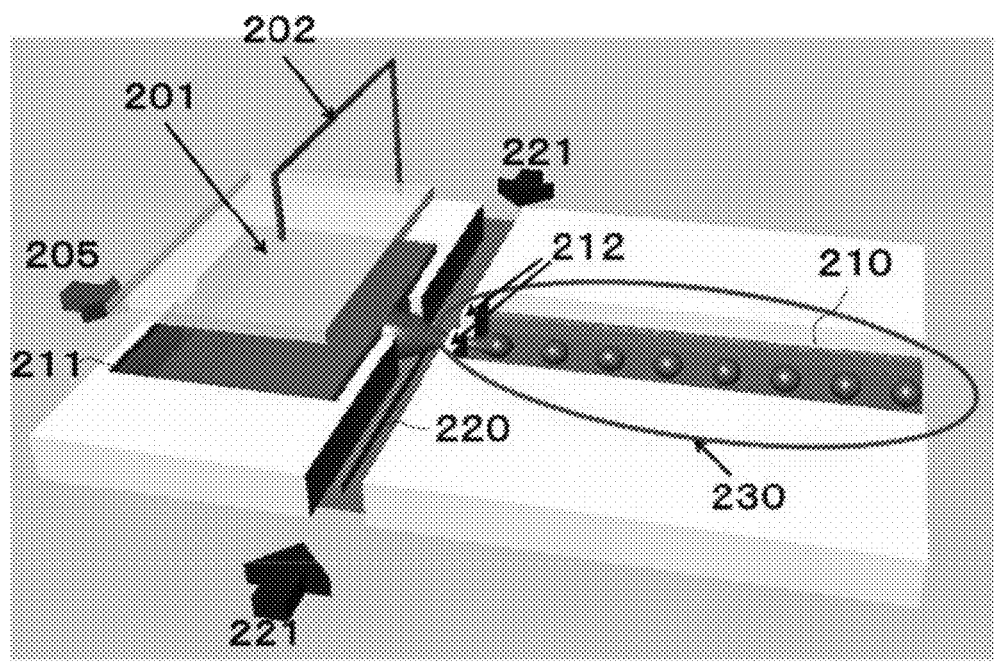
FIG. 14 is a model diagram showing a simplification of another, fourth embodiment of the plasma bubble jetting member.

There are no particular limitations as to the shape of the plasma bubble jetting member, provided that the shape is one such that high-frequency electrical pulses can be applied to an inert gas by a pair of electrodes, to push a plasma-containing inert gas into a liquid. FIG. 14 is a model diagram showing a simplification of another embodiment of the plasma bubble jetting member. In the plasma bubble jetting member of the fourth embodiment, the section where the plasma is generated within the microscopic flow passage 210 of the plasma bubble jetting member shown in FIG. 11 is formed to be larger than other sections, creating a plasma reservoir 211 for holding the inert gas containing the plasma generated through application of high-frequency electrical pulses. The pair of electrodes are plate-shaped, an electrode 201 and the other plate-shaped electrode, not illustrated, being connected by a wire 202, and formed so as to sandwich the plasma reservoir 211 from above and below. The electrode 201 is preferably at least of a size sufficient to cover the plasma reservoir 211, in order to increase the plasma concentration. By applying high-frequency electrical pulses to the electrode 201, a plasma is generated in the inert gas 205 inflowing to the microscopic flow passage, and in the plasma bubble jetting member of the fourth embodiment, because the plasma reservoir 211 has been formed in the microscopic flow passage, and the volume of the plasma reservoir 211 is greater than the volume of the plasma-containing inert gas being pushed into the liquid flow passage 220, high-frequency electrical pulses can be applied any number of times to the plasma-containing inert gas held therein, whereby the plasma concentration in the inert gas can be increased. The plasma-containing inert gas pushed out from the plasma reservoir 211 is severed by fluid force in the course of intersecting the liquid 221 which flows through the liquid flow passage 220, and flows into the microscopic flow passage 210 in the form of a liquid containing the plasma-containing inert gas. The bubbles 230 can be formed by the fluid force of the liquid 221 alone, but bubble formation is facilitated by providing the microscopic flow passage 210 with orifices 212. By controlling the spacing of the orifices 212, the size of the bubbles 230 can be adjusted.

Figure 15:
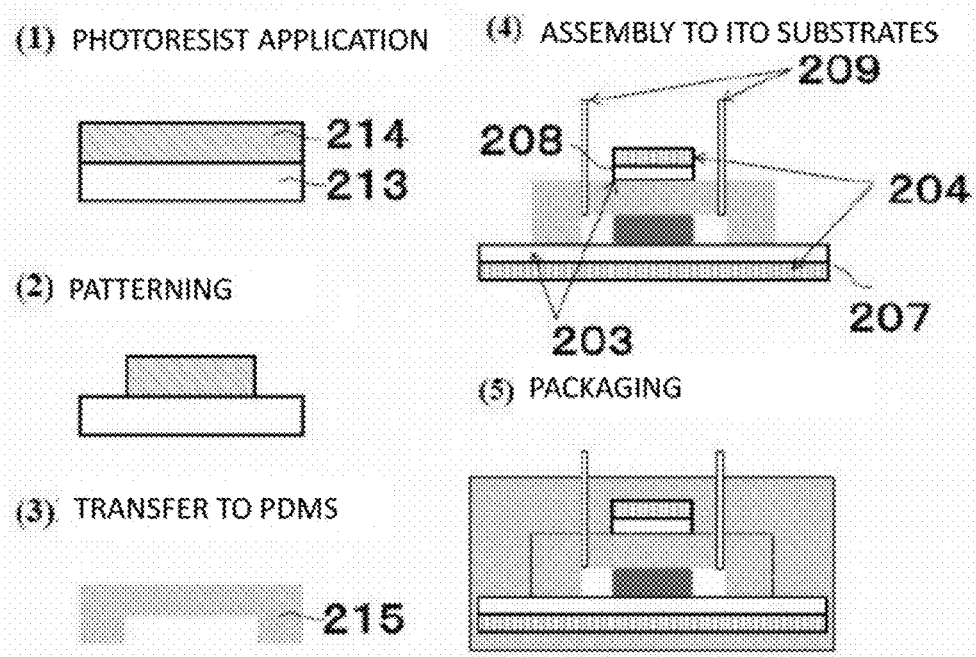
FIG. 15 (a) is a diagram showing a procedure for fabricating the plasma bubble jetting member shown in the aforementioned FIG. 14, and FIG. 15 (b) shows the plasma bubble jetting member fabricated by the procedure of FIG. 15 (a)
Figure 15:
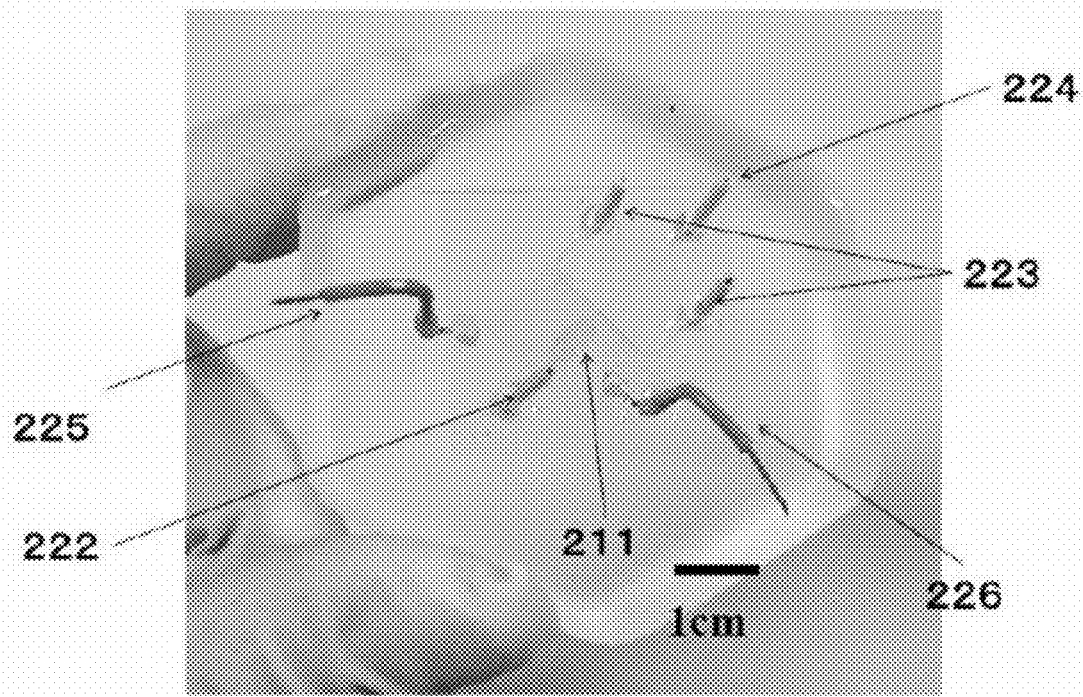

FIG. 15 (a) is a diagram showing a procedure for fabricating the plasma bubble jetting member shown in the aforementioned FIG. 14. (1) A silicon substrate 213 500 μm in thickness was spun-coated with a thick film of a negative photoresist 214 (SU-8 3050 from Nippon Kagaku Co. Ltd., 100 μm in thickness). (2) A photomask of a shape capable of patterning the microscopic flow passage 210, the plasma reservoir 211, and the liquid flow passage 220 was put on, and after irradiation with ultraviolet to pattern the SU-8, development was carried out with PM thinner (composition: PGMEA, aqueous solubility 1 g/100 g water (25° C.)), to fabricate a mold. (3) Next, polydimethyl siloxane (PDMS)

was transferred to the mold, and a PDMS flow channel part 215 having the microscopic flow passage 210, the plasma reservoir 211, and the liquid flow passage 220 was fabricated. (4) Using ITO substrates (glass part 203: 100 µm, ITO part 204: 300 nm), one was processed to 30×30 mm as a bottom substrate 207, and another to 15×15 mm as a top substrate 208, then the glass part 203 of the bottom substrate 207 and the PDMS flow channel part 215 were bonded by plasma bonding (Femto Science Inc.); and at the top face of the plasma reservoir 211 as well, the top substrate 208 was bonded, with the glass part 203 of the top substrate 208 positioned at the bottom. The glass part 203 of the ITO substrate serves as a dielectric. Thereafter, Teflon tubes 209 were inserted into the microscopic flow passage 210, the plasma reservoir 211, and the liquid flow passage 220 of the PDMS flow channel part 215, and an inert gas introduction port 222, a liquid introduction port 223, and a liquid discharge port 224 (not illustrated) were formed. Further, the ITO parts of the bottom substrate and of the top substrate were wired using a conductive paste, such as a silver paste, to carry out lower electrode wiring 225 and upper electrode wiring 226. (5) In order to prevent leakage of the liquid and fabricate a robust plasma bubble jetting member having gas-tightness for stable plasma generation, the entire chip was packaged with the same PDMS employed to fabricate the PDMS flow channel part 215. FIG. 15 (b) shows the plasma bubble jetting member fabricated by the aforedescribed procedure. The microscopic flow channel of the plasma bubble jetting member fabricated as above had a width of 200 µm, a depth of 100 µm, and a length of 2 cm, while the oval-shaped plasma reservoir section had a 7 mm major axis and a 3 mm minor axis. The liquid channel was 200 µm wide and 100 µm deep.

Figure 16:
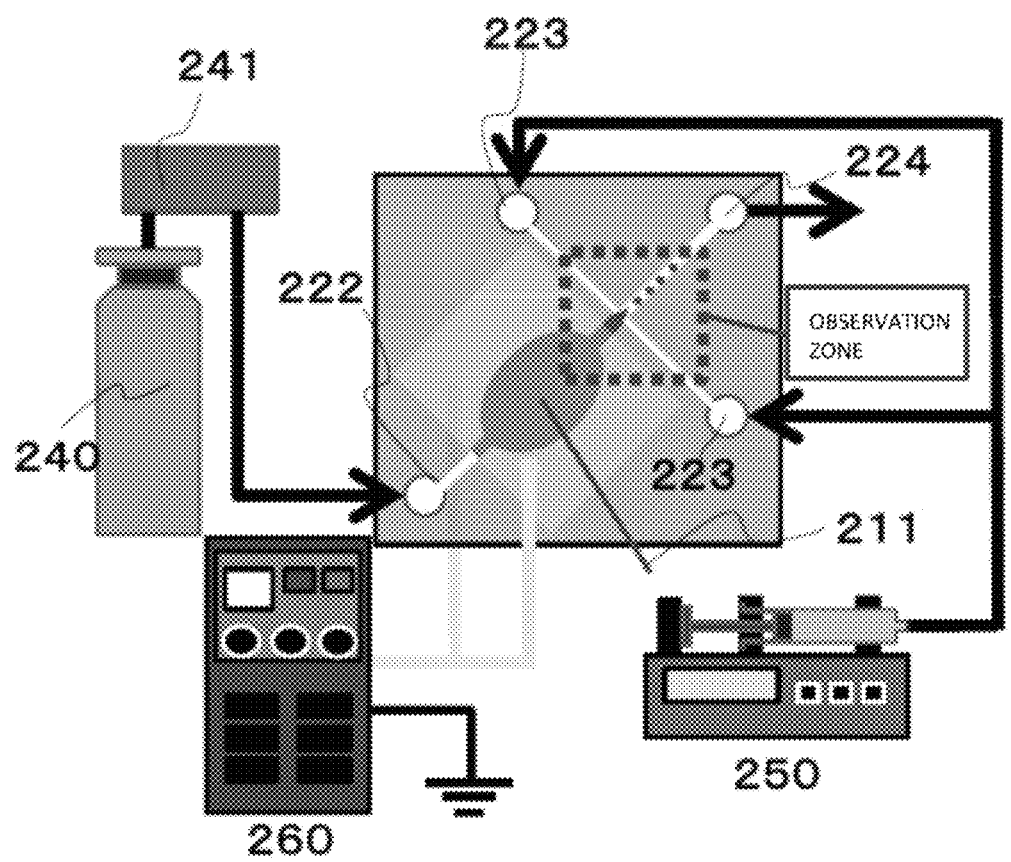
FIG. 16 is a simplified schematic diagram showing an example of a localized ablation device and therapeutic device employing the plasma bubble jetting member of the present invention.

FIG. 16 is a simplified schematic diagram showing an example of a localized ablation device and therapeutic device employing the plasma bubble jetting member of the present invention. In the present invention, "therapy" refers to medical treatment of biological tissue by directing plasma-containing bubbles thereagainst, for the purpose of killing malignant cells such as cancer or the like, activating cells, or carrying out disinfection, sterilization, or the like. Using the device shown in FIG. 16, an experiment was carried out to confirm that the plasma-containing bubbles maintained the plasma state in a liquid. The plasma bubble jetting member shown in FIG. 15 (b) was employed. Using a needle valve 241 equipped with a flow meter, helium gas was delivered from a gas cylinder 240, adjusting the flow rate to $Q_g$=0.20 ml/h. Water used as the liquid was fed in by a syringe driver 250, adjusting the flow rate to $Q_l$=200 ml/h. A high-speed, high-voltage power supply 260 (MPP-HV30 from Kurita Seisakusho Co. Ltd.) was used as the power supply. The output power was ±1-4 kV, the output current was 5 A, the repetition frequency was 30 kHz, and the output pulse width was 1-4 µs.

Figure 17:
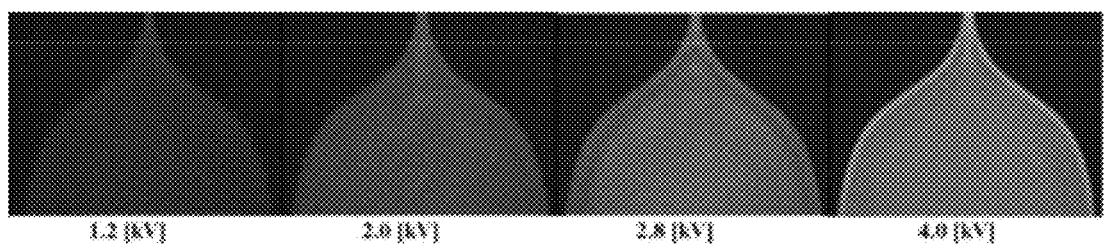
FIG. 17 is a photograph substituting for a drawing, and is an optical microscopic photograph showing stable generation of a plasma within a plasma reservoir 211.

FIG. 17 is an optical microscopic photograph showing stable generation of a plasma within the plasma reservoir 211. It was confirmed that a plasma could be generated by an applied voltage of 1.2 kV. As the applied voltage was increased further, the brightness of the plasma stabilized at 2.8 kV, and reached maximum brightness at 4.0 kV.

Meanwhile, with regard to the bubbles generated when the plasma-containing inert gas is severed by fluid force of a liquid in the intersecting liquid flow passage, it was confirmed that bubbles of a minimum diameter of 40 µm to a maximum diameter of 110 µm could be formed consistently. The flow rate ratio $Q_g/Q_l$ of the inert gas pushed into the intersecting liquid flow passage and the liquid is preferably within a range of 0.001-0.01, in order to form bubbles of the aforementioned diameter.

Figure 18:
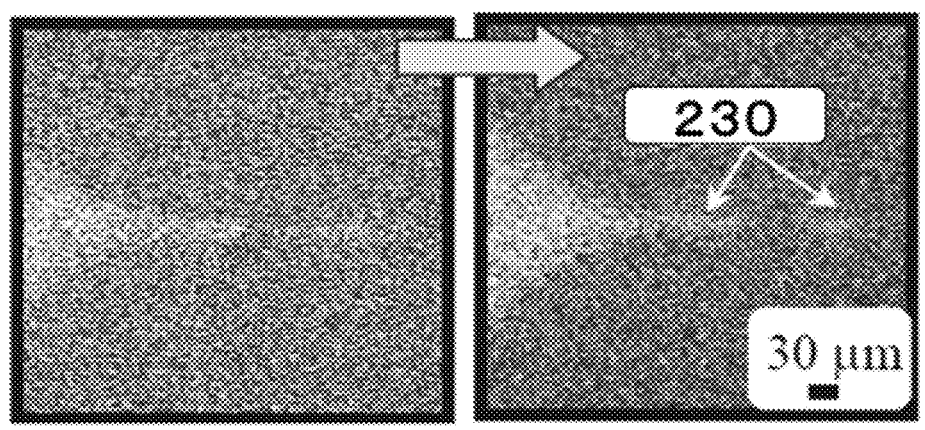
FIG. 18 shows photographs substituting for a drawing, which are photographs taken by a CCD camera, showing that even after bubbles containing plasma have formed due to fluid force, the bubbles maintain a plasma state in liquid.

FIG. 18 shows photographs taken by a CCD camera, showing that even after bubbles containing plasma have formed due to fluid force, the bubbles maintain a plasma state in liquid. The test was carried out at a frequency of 30 kHz, an applied voltage of 3.5 kV, a pulse width of 3 µs, a helium introduction flow rate of $Q_g$=0.20 ml/h, and a liquid introduction flow rate of $Q_l$=200 ml/h, using a CCD camera to observe light emission by the generated bubbles under dark field conditions. It will be apparent from the photographs that the plasma reservoir 211 holding the plasma-containing helium gas is bright, and moreover bubbles 230 ejected into the liquid from the plasma reservoir 211 and formed by fluid force are bright as well, thus confirming that the plasma-containing bubbles maintained a state of containing plasma, even in liquid. Consequently, by positioning, for example, a cell or other biological tissue in the direction of bubble advance, localized ablation can be carried out by the bubbles, and therapy of biological tissue by the plasma contained in the bubbles can be accomplished.

OTHER EMBODIMENTS

While embodiments of the present invention have been described hereinabove, the present invention is not limited to these embodiments, and various other modes are possible to adopt. For example:

(1) The microscopic bubbles 60 ejected by high-frequency discharge pulses enable an injection substance to reach the cell membrane 51 or cell nucleus 45 due to the impact of cavitation. Application is also possible to improve the efficiency of introduction of genes or the like into plant cells or other such cells having rigid cell walls resulting in low introduction efficiency; or in patterning/process techniques by the ejected microscopic bubbles 60, through external control of the electric field around the tip part of the outside shell part 21.

(2) It is possible to attach the localized ablation device to a generic microscope manipulator, endoscope, or other generic medical instruments, making possible therapy through introduction of drugs. Meanwhile, in the field of phase boundary elemental technology, there are potential applications for directional bubble streams in localized phase boundary reactions of gas/liquid phase boundaries, in crystallization techniques during bubble collapse, and the like.

It is also possible to adopt the following modes for the present invention: a cutting tool; a localized ablation method; a localized ablation device; or an injection method.

(1) A cutting tool, comprising: a core formed from a conductive material; an inner part of an extended section of an insulating material covering the core and extending for a predetermined length from the tip of the core; a shell part formed to have a space in relation to the tip of the core; and an electrode part situated outside the shell part, and that together with the core, constitutes a pair of electrodes.

(2) The cutting tool according to (1), wherein the core and the shell part are characterized as formed by passing a conducting wire or other conducting material through an inner part of a hollow tube formed from glass or other insulating material, and in this state, heating and pulling apart a portion thereof from both ends, whereby due to a difference in viscoelasticity between the glass or other insulating material and the conducting wire or other conducting material, the space forms to the inside of the shell part, in relation to the tip of the core.

(3) A localized ablation method, wherein: the cutting tool according to (1) or (2) is immersed in a liquid phase; a high-frequency voltage is applied by a high-frequency power supply, across the electrode and the core of the cutting tool immersed in a liquid phase; and through application of the high-frequency current, bubbles held in the space of the cutting tool are ejected in a directional bubble stream from the tip of the core towards the electrode.

(4) The localized ablation method according to (3), wherein the localized ablation method is characterized in that a process target is placed between the core and the electrode, and the process target is treated by a bubble stream ejected towards the electrode from the core.

(5) A localized ablation method, wherein: the electrode and the core of the cutting tool according to (1) or (2) are situated on an inside wall face of a microscopic flow passage, and an inert gas is flowed between the electrode and the core; an ionized gas phase or plasma is generated within the microscopic flow passage through application of a high-frequency voltage across the electrodes; and a gas-liquid phase boundary encapsulating or partially encapsulating an ionized gas phase, active gas phase, or plasma state within a liquid is generated through intersection with a microscopic flow passage situated adjacently to the microscopic flow passage, and through which a liquid flows.

(6) A localized ablation device, comprising:
a core formed from a conductive material; an inner part of an extended section of an insulating material covering the core and extending for a predetermined length from the tip of the core; a shell part formed to have a space in relation to the tip of the core; an outside multilayered shell part having an axis coaxial with the center axis of the shell part, formed by multiple layers to the outside of the shell part, and formed such that a substance for injection may be introduced; and an electrode part situated outside the shell part, or at a location immersed in a liquid phase within the outside multilayered shell part, and that together with the core, constitutes a pair of electrodes.

(7) The localized ablation device according to (6), wherein the shell part and the outside multilayered shell part are characterized as formed by heating and pulling apart from both ends a portion of a hollow tube formed from an insulating material, and with the shell part having the core being designated as the center axis, arranging the outside multilayered shell part superimposed to the outside thereof so as to be coaxial to the center axis, forming a mechanism for sealing an injection substance within the outside multilayered shell part.

(8) An injection method, comprising: introducing an injection substance into the interior of an outside multilayered shell part of the localized ablation device according to (6) or (7); applying a high-frequency voltage from a high-frequency power supply across the core and the electrode part of the injection device while immersed in a liquid phase; through the application of a high-frequency voltage by the high-frequency power supply, ejecting bubbles held in the space of the shell part, and having at the phase boundary thereof an injection substance introduced by the outside multilayered shell part, in a directional bubble stream from tip of the core; and causing cavitation of the bubbles to occur at the process target surface to treat the process target surface, while simultaneously causing injection of the substance contained on the phase boundary to occur from the treated face.

(9) The injection method according to (8), wherein: the injection substance introduced by the outside multilayered shell part is a substance in the liquid phase, gas phase, or solid phase; the method of introduction of the injection substance is a method employing a pump to feed from the outside multilayered shell part, or a method whereby the injection substance is suctioned through capillary action into the outside multilayered shell part only, while immersed therein; and simultaneously with the bubbles collected in the space in relation to the center axis of the outside multilayered shell part being ejected through discharge by application of an electrical pulse to the core, the liquid phase present in relation to the center axis of the outside multilayered shell part is drawn out through fluid force, in amounts that can be adsorbed onto the phase boundaries, thereby effecting injection.

(10) The localized ablation and injection method according to (8) or (9), wherein subsequent to injection, the electrode part is separated from the target and any treated proteins or impurities deposited around the tip of the outside multilayered shell part rear part are swept away by an electrical discharge, to thereby carry out injection intermittently on multiple targets.

(11) The injection method according to any of (8) to (10), wherein an oscillator is installed in the outside multilayered shell part and compressional waves are generated, whereby only a single bubble at a specific position in the bubble stream generated by electrical discharge of the core is collapsed at a location at which the generated compressional waves overlap.

REFERENCE SIGNS LIST 5 microbubble stream
10 fabrication method of bubble jetting member having space at tip
15 insulating material
16 shell part
20 core (conducting material)
21 outside shell part
22 space
23 coaxial positioning washer
24 hole
25 heat
26 pulled apart glass tube
27 guide
30 space
35 counter electrode
40 biomaterial (bovine egg)
45 nucleus
50 zona pellucida
51 cell membrane
52 ejection phase boundary
53 process width
55 gas/liquid phase boundary
60 bubble
61 solution containing injection substance
62 bubble shape under pressure disequilibrium
63 microjet
64 hole
65 active electrode (core 20)
70 ordinary commercial AC power supply unit
71 counter electrode
75 non-inductive resistance
80 voltage amplification circuit
85 capacitor
85 conductive solution (culture broth or the like)
90 glass capillary
91 fluorescent beads
92 suction pipette 93 cell wall
95 removal area
100 oscillator
105 compressional waves
110 overlapping part of compressional waves
200 counter electrode (nickel electrode)
201 pair of electrodes (plate-shaped)
202 wire
203 glass substrate (dielectric)
204 ITO substrate (conductor)
205 inert gas (nitrogen or helium gas)
207 bottom substrate
208 top substrate
209 Teflon tube
210 microscopic flow passage
211 plasma reservoir
212 orifice
213 silicon substrate
214 photoresist
215 PDMS flow channel part
220 liquid flow channel
221 liquid
222 inert gas introduction port
223 liquid introduction port
224 liquid discharge port
225 lower electrode wiring
226 upper electrode wiring
230 bubble containing plasma
240 gas cylinder
241 needle valve equipped with a flow meter
250 syringe driver
260 high-speed, high-voltage power supply

What is claimed is:

1. A device comprising a plasma bubble jetting member, comprising:
   a substrate;
   a pair of electrodes formed from a conducting material, and adapted for generating a plasma in an inert gas;
   a liquid flow passage on the substrate through which a liquid flows; and
   a microscopic flow passage on the substrate comprising a first portion through which flows an inert gas and which contains the pair of electrodes, and a second downstream portion through which flows an inert gas, an inert gas containing a plasma, and a liquid containing bubbles of an inert gas containing a plasma;
   the liquid flow passage and the microscopic flow passage connecting at a downstream side from a section in which the plasma is generated in the microscopic flow passage.

2. The device according to claim 1, wherein the microscopic flow passage includes a plasma reservoir in which the section in which the plasma is generated is made larger than the rest of the microscopic flow passage.

3. The device of claim 2 which is a localized ablation device.

4. A localized ablation or therapeutic method, comprising:
   causing an inert gas to flow into a microscopic flow passage of a device comprising a plasma bubble jetting member which comprises:
      a substrate;
      a pair of electrodes formed from a conducting material, and adapted for generating a plasma in an inert gas;
      a liquid flow passage on the substrate through which a liquid flows; and
      a microscopic flow passage on the substrate comprising a first portion through which flows an inert gas and which contains the pair of electrodes, and a second downstream portion through which flows an inert gas, an inert gas containing a plasma, and a liquid containing bubbles of an inert gas containing a plasma;
   the liquid flow passage and the microscopic flow passage connecting at a downstream side from a section in which the plasma is generated in the microscopic flow passage;
   applying a high-frequency electrical pulse to the pair of electrodes to generate a plasma in the inflowing gas;
   causing the inert gas containing the plasma to flow into a liquid in the liquid flow channel which connects to the microscopic flow passage, to generate bubbles containing plasma; and
   (a) processing a target with the bubbles containing plasma to effect localized ablation or (b) effecting therapy of the biological tissue with the bubbles containing plasma.

5. The device of claim 2 which is a therapeutic device.

6. The device according to claim 2, wherein the electrode is of a size at least sufficient to cover the plasma reservoir.

7. The device of claim 6 which is a localized ablation device.

8. The localized ablation or therapeutic method of claim 4, wherein the microscopic flow passage includes a plasma reservoir in which the section in which the plasma is generated is made larger than the rest of the microscopic flow passage.

9. The device of claim 6 which is a therapeutic device.

10. The device of claim 1 which is a localized ablation device.

11. The localized ablation or therapeutic method of claim 8, wherein the electrode is of a size at least sufficient to cover the plasma reservoir.

12. The device of claim 1 which is a therapeutic device.

13. A plasma bubble jetting member, comprising:
   a substrate;
   a pair of electrodes formed from a conducting material, and adapted for generating a plasma in an inert gas;
   a liquid flow passage on the substrate through which a liquid flows; and
   a microscopic flow passage on the substrate comprising a first portion extending through a center flow direction axis and through which flows an inert gas, and which contains the pair of electrodes, and a second downstream portion through which flows an inert gas, an inert gas containing a plasma, and a liquid containing bubbles of an inert gas containing a plasma along the center flow direction axis,
   wherein the liquid flow passage connects and merges with the microscopic flow passage at a downstream side on the center flow direction axis from a section in which the plasma is generated in the microscopic flow passage.

14. The device according to claim 1, wherein in the plasma bubble jetting member an angle of a section in which the microscopic flow passage and the liquid flow passage connect is at least greater than 0 degrees but not more than 90 degrees.

15. The device according to claim 14, wherein an angle of a section in which the microscopic flow passage and the liquid flow passage connect is 20-90 degrees.

16. The device according to claim 1, wherein in the plasma bubble jetting member two or more fluid flow channels are formed.

* * * * *